(12) United States Patent
Bennett et al.

(10) Patent No.: US 9,403,862 B2
(45) Date of Patent: Aug. 2, 2016

(54) REAGENT CONTROLLED STEREOSELECTIVE GLYCOSYLATION

(71) Applicant: Trustees of Tufts College, Boston, MA (US)

(72) Inventors: Clay S. Bennett, Somerville, MA (US); John P. Issa, Medford, MA (US); Dina Lloyd, Concord, NH (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 14/445,917

(22) Filed: Jul. 29, 2014

(65) Prior Publication Data

US 2015/0038689 A1   Feb. 5, 2015

Related U.S. Application Data

(60) Provisional application No. 61/946,289, filed on Feb. 28, 2014, provisional application No. 61/886,915, filed on Oct. 4, 2013, provisional application No. 61/860,010, filed on Jul. 30, 2013.

(51) Int. Cl.
  *C07H 1/00* (2006.01)
  *C07H 5/10* (2006.01)
  *C07H 15/18* (2006.01)
  *C07H 15/207* (2006.01)
  *C07H 9/04* (2006.01)

(52) U.S. Cl.
  CPC . *C07H 1/00* (2013.01); *C07H 15/18* (2013.01)

(58) Field of Classification Search
  None
  See application file for complete search history.

(56) References Cited

U.S. PATENT DOCUMENTS

2014/0303359 A1    10/2014 Bennett et al.

OTHER PUBLICATIONS

Issa, Organic Letters 2013, vol. 15, No. 16, 4170-417, supporting information.*
Micó, Unexpected reactions and novel glycosylations with benzotriazole and nitrophenyl derivatives, Dissertation, 2006.*
Issa, J. P., et al., "Reagent Controlled 6-Specific Dehydrative Glycosylation Reactions with 2-Deoxy-Sugars", *Organic Letters*, 15(16):4170-4173 (American Chemical Society, 2013).

* cited by examiner

*Primary Examiner* — Layla Berry
(74) *Attorney, Agent, or Firm* — Dana M. Gordon; Foley Hoag LLP

(57) ABSTRACT

Provided are methods for the efficient stereoselective formation of glycosidic bonds, without recourse to prosthetic or directing groups.

22 Claims, 5 Drawing Sheets

US 9,403,862 B2

REAGENT CONTROLLED STEREOSELECTIVE GLYCOSYLATION

RELATED APPLICATIONS

This application claims benefit of U.S. Provisional Patent Application No. 61/860,010, filed Jul. 30, 2013; U.S. Provisional Patent Application No. 61/886,915, filed Oct. 4, 2013; and U.S. Provisional Patent Application No. 61/946,289, filed Feb. 28, 2014.

GOVERNMENT SUPPORT

This invention was made with government support under grant 1300334 awarded by the National Science Foundation. The government has certain rights in the invention.

BACKGROUND

Complex oligosaccharides are widely recognized to play a critical role in a host of important biological interactions including protein folding, the immune response, cellular recognition, and host-pathogen interactions. Despite their importance, our understanding of the molecular basis of carbohydrate function lags far behind our knowledge of proteomics and genomics. This is predominantly due to a scarcity of homogeneous, well-defined carbohydrates to serve as standards for glycomics analysis. Biological systems produce oligosaccharides as complex and often intractable mixtures, leaving chemical synthesis as the only avenue for the production of homogenous material for study. For a number of reasons, carbohydrate synthesis remains a formidable challenge, despite numerous advances in recent years. Among the issues which plague carbohydrate synthesis, controlling selectivity of glycosylation reactions is one of the most difficult, largely because most methods for chemical glycosylation reactions rely heavily on the substrates to control the diastereoselectivity. In many cases it is difficult to obtain the desired linkages with good selectivity without extensive modifications to both coupling partners, to obtain a "matched" pair. In the absence of native functionality that permits the introduction of directing groups, the problem is greatly magnified. Stereoelectronic effects can be used to facilitate formation of certain linkages, but to date few robust methods to synthesize difficult linkages without recourse to chiral auxiliaries, temporary prosthetic groups, or de novo synthesis exist. These latter approaches necessarily introduce additional steps into carbohydrate synthesis, and they often do not guarantee selectivity with a broad range of substrates.

Compounds comprising so-called "difficult linkages" such as β-linked 2-deoxy-sugars are often essential for the bioactivity of many natural products, including, for example, digitoxin, mithramycin, and landomycin A. Furthermore, oligosaccharides composed of deoxy-sugars have been shown to possess potent biological activity. Altering the composition of these sugars can modulate a natural product's bioactivity, potentially reducing undesirable side effects. This approach has yet to be broadly adapted to drug discovery, however, as these linkages are considered to be among the most challenging to synthesize directly.

Methods for the direct construction of β-linked phenolic glycosides and thioglycosides of 2-deoxy-sugars have been described, but reports of the direct stereoselective synthesis of β-linked 2-deoxy-sugar disaccharides and oligosaccharides are exceedingly rare. Moreover, the mechanistic basis of selectivity in these latter reactions has yet to be elucidated, and selectivity does not always translate well between systems.

Consequently, there is a pressing need for robust and selective glycosylation reactions that work with a range of carbohydrates.

SUMMARY OF THE INVENTION

The invention provides methods useful for the efficient stereoselective formation of glycosidic bonds. The invention is based, in part, on the discovery by the inventors that certain strong Bronsted bases and certain sulfonylating agents can be used to form glycosidic bonds with remarkably high stereoselectivity. Surprisingly, it is possible, in accordance with the invention, to obtain highly stereoselective glycosylation reactions without recourse to prosthetic or directing groups.

An aspect of the invention is a method of forming a glycosidic bond, the method comprising the steps of:

combining a first solvent, a reducing sugar, and a first strong Bronsted base, thereby forming a first reaction mixture;

combining a sulfonylating agent and the first reaction mixture, thereby forming a glycosyl sulfonate;

combining a second solvent, a glycosyl acceptor, and a second strong Bronsted base, thereby forming a second reaction mixture; and combining the glycosyl sulfonate and the second reaction mixture, thereby forming a glycosidic bond;

wherein the glycosidic bond is formed with greater than or equal to 90% stereoselectivity for a particular stereochemical configuration.

In an embodiment, the glycosidic bond is formed with greater than or equal to 95% stereoselectivity for a particular stereochemical configuration.

In an embodiment, the glycosidic bond is formed with greater than or equal to 98% stereoselectivity for a particular stereochemical configuration.

In an embodiment, the glycosidic bond is formed with greater than or equal to 99% stereoselectivity for a particular stereochemical configuration.

In an embodiment, the reducing sugar is a 2-deoxy-sugar.
In an embodiment, the reducing sugar is a pyranose.
In an embodiment, the reducing sugar is a furanose.
In an embodiment, the reducing sugar is a D-sugar.
In an embodiment, the reducing sugar is an L-sugar.
In an embodiment, the reducing sugar is a D-sugar; and the particular stereochemical configuration is a β linkage.
In an embodiment, the reducing sugar is an L-sugar; and the particular stereochemical configuration is a β linkage.

In an embodiment, the first strong Bronsted base is selected from the group consisting of: sodium tert-butoxide, potassium tert-butoxide, lithium tert-butoxide, lithium diisopropylamide, lithium tetramethylpiperidide, sodium hexamethyldisilazane (NaHMDS), and potassium hexamethyldisilazane (KHMDS).

In an embodiment, the second strong Bronsted base is selected from the group consisting of: sodium tert-butoxide, potassium tert-butoxide, lithium tert-butoxide, lithium diisopropylamide, lithium tetramethylpiperidide, sodium hexamethyldisilazane (NaHMDS), and potassium hexamethyldisilazane (KHMDS).

In an embodiment, the first strong Bronsted base is same as the second strong Bronsted base.

In an embodiment, the sulfonylating agent is selected from the group consisting of: sulfonic anhydrides, sulfonyl halides, and N-sulfonylimidazoles.

In an embodiment, the sulfonylating agent is p-toluenesulfonic anhydride.

In an embodiment, the glycosyl acceptor is a monosaccharide, a disaccharide, an oligosaccharide, or a polysaccharide, each comprising at least one —OH, —SH, or primary or secondary amino group.

DETAILED DESCRIPTION OF THE INVENTION

Figure 1A:
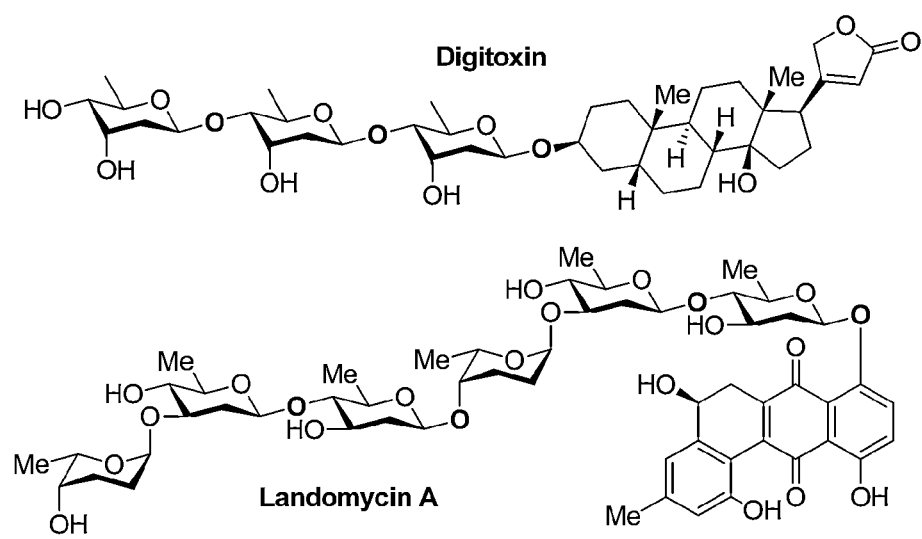
FIG. 1A depicts representative biologically active natural products containing β-glycosidic deoxy-sugar linkages.

As part of an ongoing program aimed at developing selective methods for 2-deoxy-sugar synthesis, we chose to examine the in situ generation of different glycosyl sulfonates for β-selective glycosylations. While glycosyl triflates can undergo $S_N2$-like reactions to afford β-linked products with certain substrates, Crich has shown that 2-deoxy glycosyl triflates are generally very unstable. Crich, D.; Vinogradova, O. *J. Org. Chem.* 71:8473-8480 (2006). Furthermore, it has been reported that even in examples where 2-deoxy-sugar triflates are not subject to decomposition, they only undergo β-selective reactions when strong carbon nucleophiles are employed as acceptors. Krumper, J. R. et al., *Org. Lett.* 10:4907-4910 (2008); Krumper, J. R. et al., *J. Org. Chem.* 74:8039-8050 (2009). In principle, a more stable sulfonate should possess greater covalent character, permitting direct $S_N2$ displacement to afford the product as a single diastereomer. While the reactivity of different sulfonates has been reported to span several orders of magnitude, little work has been done on glycosyl sulfonates other than triflates since the seminal studies of the Schuerch and Koto groups over three decades ago. Eby, R. et al., *Carbohydr. Res.* 34:79-90 (1974); Koto, S. et al., *Chem. Lett.* 587-588 (1975); Lucas, T. J. et al., *Carbohydr. Res.* 39:39-45 (1975); Maroušek, V. et al., *Carbohydr. Res.* 60:85-96 (1978); Srivastava, V. K. et al., *Carbohydr. Res.* 79:Cβ-C16 (1980); Koto, S. et al., *Bull Chem. Soc. Jpn.* 53:1761-1762 (1980); Srivastava, V. K. et al., *J. Org. Chem.* 46:1121-1126 (1981). This is due to the fact that many of these procedures required the isolation of highly unstable species. Additionally, those procedures for in situ generation of sulfonates often led to non-selective reactions. The lack of selectivity is presumably due to the presence of several other nucleophilic ions in solution, which could scramble the stereochemistry of the anomeric leaving group.

To address these issues, N-sulfonylimidazoles were examined as reagents for converting hemiacetals into glycosyl sulfonates in situ (Scheme 1). These species have been reported to promote sulfonate ester formation and nucleotide coupling without the generation of nucleophilic byproducts. Importantly, the synthesis of N-sulfonylimidazoles is trivial, which would permit the rapid synthesis of a large library of compounds to tune reactivity.

Scheme 1. N-sulfonylimidazoles for β-selective glycosylation

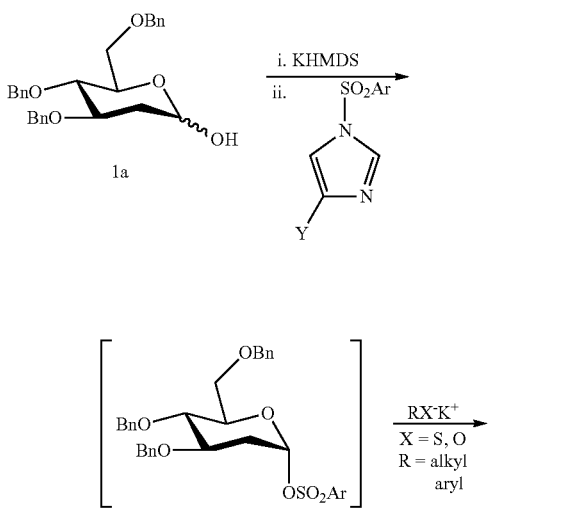

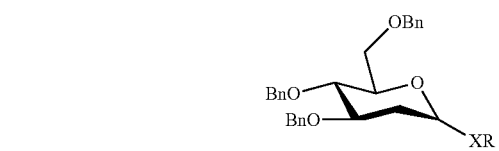

Initial investigations focused on thiol nucleophiles, owing to both their increased reactivity and the fact that thioglycoside linkages are useful non-hydrolyzable carbohydrate mimetics. To this end, deprotonation of 1a with KHMDS in THF at low temperature was followed first by addition of N-tosylimidazole (TsIm), then the nucleophile. The selectivity in the reaction was dependent on the amount of time 1a was allowed to react with the TsIm (Table 1, entries 1-3). Longer reaction times generally led to higher selectivity. Without meaning to be bound to any particular theory or mechanism, we believe the change in selectivity is a result of the rapid formation of a mixture of glycosyl tosylates followed by equilibration to the more stable α-anomer.

TABLE 1

Reaction Optimization with Sulfur Nucleophiles

| entry | PhSH (equiv) | Y | time (min) | yield (%) | α:β |
|---|---|---|---|---|---|
| 1 | 1 | H | 0 | 40 | 1:1 |
| 2 | 1 | H | 30 | 40 | 1:2 |
| 3 | 1 | H | 65 | 40 | 1:5 |
| 4 | 1 | $NO_2$ | 60 | 62 | β only |
| 5 | 0.67 | $NO_2$ | 60 | 88 | β only |
| 6[a] | 0.67 | $NO_2$ | 60 | 77 | β only |

[a] An equivalent of potassium imidazolide was added to the reaction.

In order to improve the yield of the reaction, the more reactive leaving group found in tosyl 4-nitroimidazole ($TsImNO_2$) was examined. Not only did this reagent improve the yield of the reaction, but a dramatic increase in selectivity from 5:1 β:α to essentially all β (i.e., >90%) was observed (Table 1, entry 4). Finally, the use of a slight excess of the activated donor led to a further increase in yield without compromising selectivity (88%, β only, Table 1, entry 5).

To determine if the lower selectivity observed with TsIm was due to the presence of imidazole interfering with the reaction, the reaction using $TsImNO_2$ was repeated in the presence of an equivalent of potassium imidazolide (Table 1, entry 6). No change in selectivity was observed, indicating that imidazole was only acting as a leaving group. Without meaning to be bound to any particular theory or mechanism, the inventors believe the lower selectivity with TsIm is a result of incomplete conversion of the donor to the glycosyl sulfonate prior to the addition of the acceptor. If acceptor is present before the sulfonate can equilibrate to the more stable α configuration, β-sulfonates will be present and react to reduce selectivity.

The scope of the reaction was next examined with several thiol acceptors (Table 2). For aliphatic thiol acceptors it was found to be helpful to use the potassium salt to obtain useful yields. Yields were generally moderate-to-good, with the secondary galactose derived thiol 4 providing the highest yield. In the case of primary thiol 6 the reaction was accompanied by significant amounts of disulfide bond formation, despite efforts to rigorously exclude oxygen from the reaction. In every single case, however, the reaction provided the product essentially as a single β-anomer, as determined by $^1H$ NMR.

TABLE 2

Scope with Thiol Acceptors

| entry | RSK | product | yield (%) | α:β |
|---|---|---|---|---|
| 1 | 3 | 7 | 41 | β only |
| 2 | 4 | 8 | 80 | β only |
| 3 | 5 | 9 | 45 | β only |
| 4 | 6 | 10 | 50 | β only |

Having established that the reaction was effective with thiolates, we turned our attention to phenoxide nucleophiles, since aryloxy glycosides are an important structural motif in many natural products. The reaction of 1 with $TsImNO_2$, followed by the addition of the potassium salt of 2-naphthol (prepared by treating the acceptor with KHMDS), provided the desired product as a single anomer as determined by $^1H$ NMR (Table 3, entry 1). Rationalizing that a solvent which could better coordinate the counterion could provide the product in enhanced yield, the use of diglyme as additive was next examined. Pleasingly, this led to an increase in the yield, affording the product in 76% as a single anomer (Table 3, entry 2). Under these conditions no glycal formation was observed, indicating that elimination of the active leaving group was not a competitive pathway. Other phenolic acceptors reacted in moderate-to-good yield, with electron-rich phenols providing the best yields.

TABLE 3

Scope with Aryloxy Acceptors

| entry | ArOK | solvent | product | yield (%) | α:β |
|---|---|---|---|---|---|
| 1 | 2-Naphthol | THF | 11 | 43 | β only |
| 2 | 2-Naphthol | diglyme | 11 | 76 | β only |
| 3 | 1-Naphthol | diglyme | 12 | 70 | β only |
| 4 | PhOK | diglyme | 13 | 67 | β only |
| 5 | o-Cresol | diglyme | 14 | 62 | β only |
| 6 | p-MeO—PhOK | diglyme | 15 | 74 | β only |
| 7 | p-CF$_3$—PhOK | diglyme | 16 | 45 | β only |

The more reactive 2,6-dideoxy-L-arabino hexopyranose donor 1b (Table 4) was also studied. Again no glycal formation was observed. Interestingly, electron-rich phenols were less effective than electron-poor phenols with this substrate, representing a reversal of the trend observed in Table 3. While the lower yields can be attributed to be due in part to the decreased stability of the 2,6-dideoxy-sugars products, the origin of this reversal in reactivity trends is unclear at this point. Importantly however, the reactions again afforded the products essentially exclusively as β-anomers, despite the fact that the absolute configuration of the donor had been switched from D- to L-. These observations support our hypothesis that TsImNO$_2$ activates the hemiacetal donors as α-glycosyl tosylates, which react through an S$_N$2-like manifold to afford β-linked products.

TABLE 4

Reactions with 2,6-Dideoxy Donors

| entry | ArO$^-$K$^+$ | product | yield (%) | α:β |
|---|---|---|---|---|
| 1 | 2-Naphthol | 18 | 41 | β only |
| 2 | 1-Naphthol | 19 | 53 | β only |
| 3 | PhOK | 20 | 73 | β only |
| 4 | o-Cresol | 21 | 56 | β only |
| 5 | p-MeO—PhOK | 22 | 63 | β only |
| 6 | p-CF$_3$—PhOK | 23 | 71 | β only |

With aliphatic aliphatic acceptors, our preliminary investigations again focused on using the tosyl imidazole reagents. Activation of the potassium alkoxide of hemiacetal 1a with N-tosyl-4-nitroimidazole and subsequent addition of the primary alkoxide acceptor 102a led to the formation of the desired disaccharide 103a in moderate yield (57%), essentially as a single β-anomer (Table 5, entry 1). Attempts to improve this yield by adjusting the donor and acceptor stoichiometry, reaction temperature, and the sulfonylating agents employed proved to be ineffective (Table 5, entries 2-6). Reasoning that a more potent sulfonylating agent would permit higher yields through more complete conversion of the hemiacetal to the glycosyl sulfonate at low temperature, we turned our attention to p-toluenesulfonic anhydride. These conditions afforded product 103a in 83% yield essentially as a single anomer (Table 5, entry 7).

TABLE 5

Optimization Studies for β-Specific Glycosylation

| entry | donor equiv. | acceptor equiv. | sulfonylating agent | temp (° C.) | yield (%) | α:β |
|---|---|---|---|---|---|---|
| 1 | 1.5 | 1.0 | A | −78 | 57 | β only |
| 2 | 3.0 | 1.0 | A | −78 | 45 | β only |
| 3 | 3.0 | 1.0 | A | −100 | 55 | β only |
| 4 | 1.5 | 3.0 | A | −78 | 42 | β only |

TABLE 5-continued

| 5 | 1.5 | 1.0 | B | −78 | 25 | β only |
| 6 | 1.5 | 1.0 | C | −78 | trace | — |
| 7 | 1.5 | 1.0 | D | −78 | 83 | β only |

Sulfonylating Agents

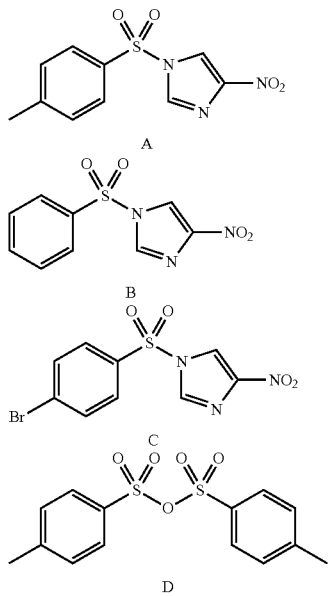

Figure 2A:
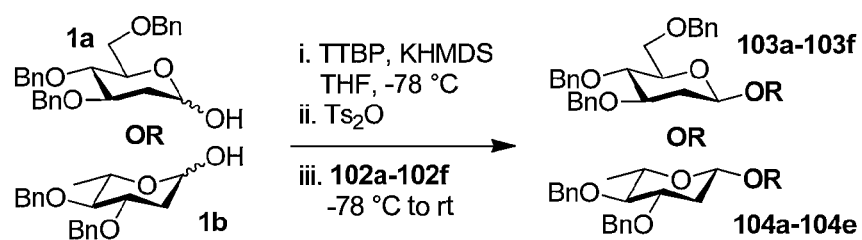
FIG. 2A depicts a general reaction scheme for p-toluenesulfonic anhydride activation with deoxy-donors.
Figure 2B:
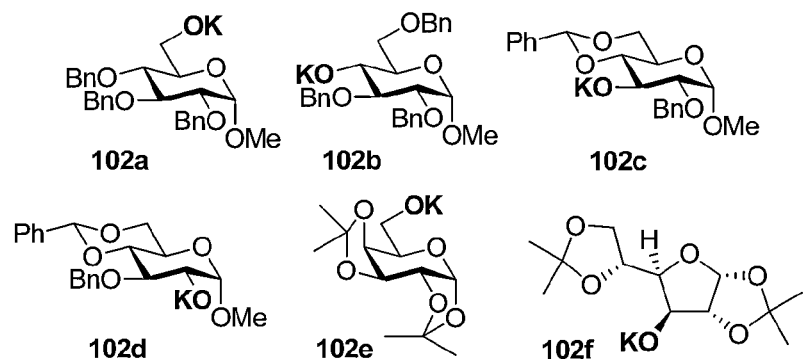
FIG. 2B depicts certain acceptor substrates described herein.
Figure 2C:
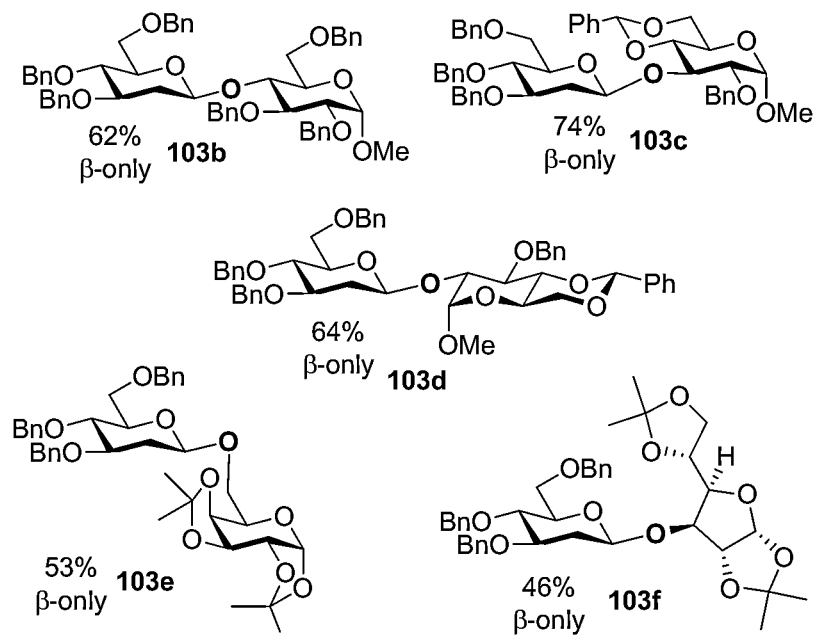
FIG. 2C depicts certain products from 2-deoxy-D-sugar donors.

Having established highly favorable reaction conditions, we turned our attention to the scope of the glycosylation. The 3,4,6-tri-O-benzyl-2-deoxy-D-glucose "armed" hemiacetal donor reacted smoothly with hindered secondary alcoholic acceptors 102b-102d (FIG. 2B) to afford products 103b-103d in good yields (62-74%). Importantly, all of the reactions proceeded with essentially complete β-stereoselectivity (FIG. 2C). Surprisingly, acceptors possessing acetonides afforded products 103e and 103f in lower yields, despite the basic nature of the reaction conditions. The reactions were still highly stereoselective, however, indicating that these groups do not interfere with the selectivity of the reaction.

Figure 2D:
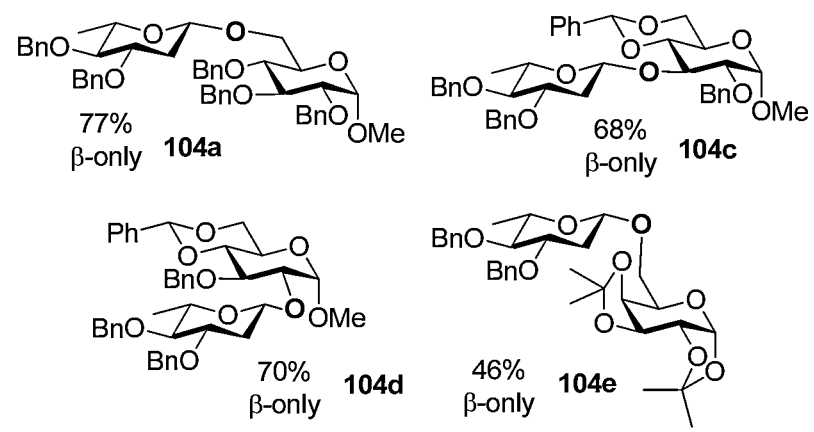
FIG. 2D depicts certain products from 2,6-dideoxy-L-sugar donors.

We next examined the more reactive 2,6-dideoxy-L-arabino hexopyranose donor 1b, which represents a common motif in many bioactive natural products. Under these conditions, elimination was once again not a problem, and we were able to obtain β-linked products with a very high degree of stereoselectivity (FIG. 2D). The primary glucose-derived alcoholic acceptor 102a reacted to afford 104a in 77% yield, while the more hindered secondary acceptors 102c and 102d afforded products 104c and 104d in 68% and 70% yield, respectively. Again, acetonide-protected acceptor 102e was less effective in the reaction, providing disaccharide 104e in moderate yield (46%).

Figure 1B:
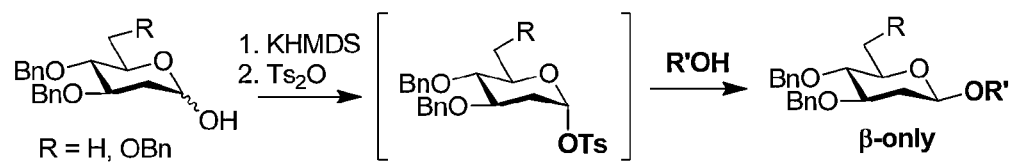
FIG. 1B depicts activation of 2-deoxy and 2,6-dideoxy donors as glycosyl p-toluenesulfonates for β-specific glycosylation.

If the reaction were proceeding through an $S_N1$-manifold, changing the absolute configuration of one of the coupling partners would be expected to alter its stereochemical outcome. Since both D- and L-configured deoxy-donors react to form essentially exclusively β-linked products, this study demonstrates that the reaction is not subject to stereochemical "match" and "mismatch" between donors and acceptors of different configurations. Without meaning to be bound to any particular theory or mechanism, the studies outlined in FIG. 1 point to the reaction proceeding through the intermediacy of an α-glycosyl tosylate that reacts through an $S_N2$-manifold. Furthermore, the data supports our hypothesis that the stereochemical outcome of the reaction is entirely under control of the promoter.

Figure 3:
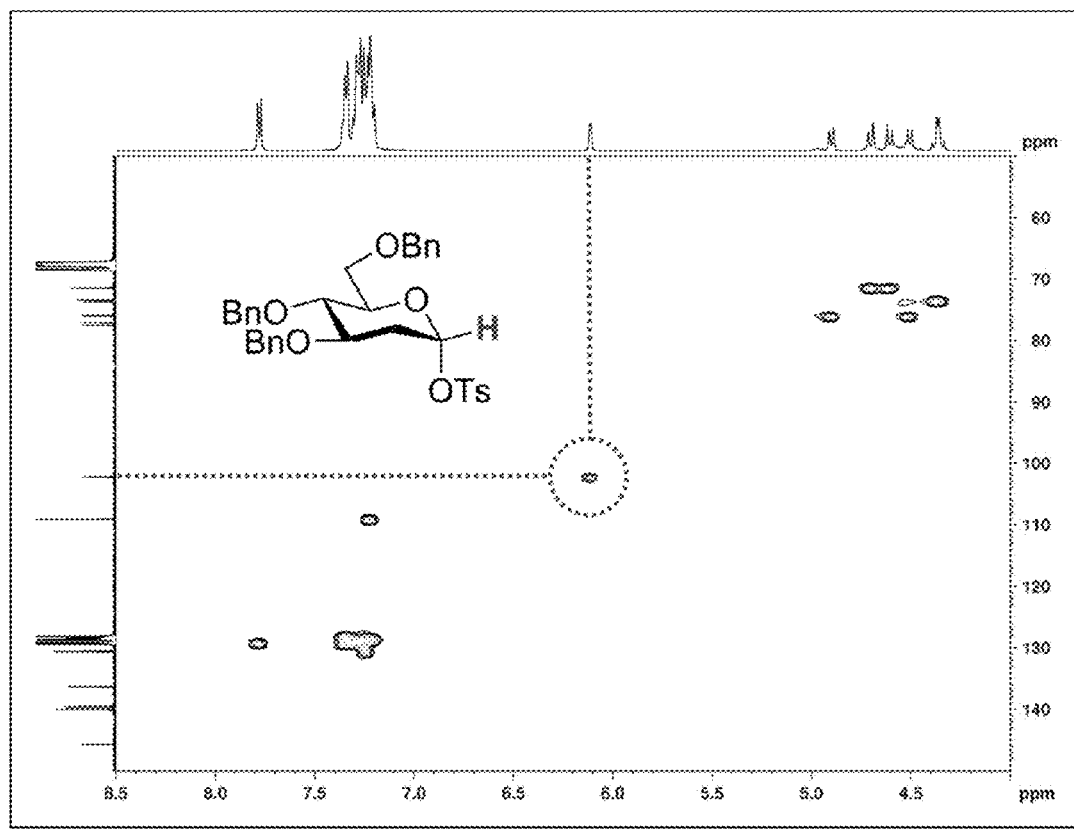
FIG. 3 depicts a heteronuclear single-quantum correlation (HSQC) 2D-NMR spectrum of α-glucosyl tosylate taken at −78° C. Lines leading to the central peak indicate the correlation between the $^{13}C$ signal for the anomeric carbon at δ 102.3 ppm and the $^1H$ signal for the anomeric proton at δ 6.11 ppm.
Figure 4:
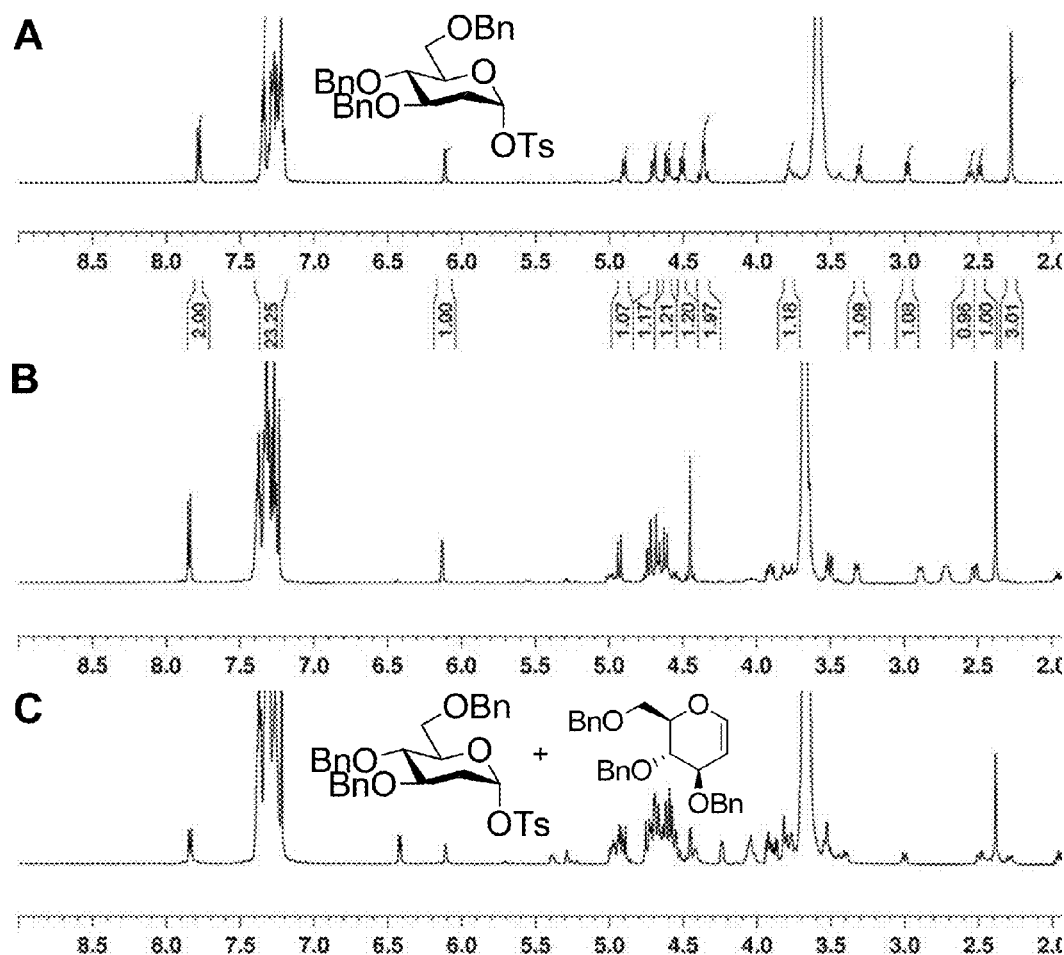
FIG. 4A depicts a $^1H$ NMR spectrum of the α-glucosyl toluenesulfonate in THF-$d_8$ at 500 MHz at −78° C.; a single compound is present in the spectrum.
FIG. 4B depicts a $^1H$ NMR spectrum of the α-glucosyl toluenesulfonate in THF-$d_8$ at 500 MHz at −5° C.; the spectrum begins to show trace elimination of the tosylate to the corresponding glucal.
FIG. 4C depicts a $^1H$ NMR spectrum of the α-glucosyl toluenesulfonate in THF-$d_8$ at 500 MHz at 25° C.; significant glucal is present.

In order to establish the intermediacy of an α-glycosyl tosylate, we turned to low-temperature NMR. Treating the potassium alkoxide of hemiacetal 1a with p-toluenesulfonic anhydride at −78° C. resulted in the quantitative formation of a new species possessing a broad singlet in the $^1$H NMR spectrum with a chemical shift of δ 6.11 ppm. This is consistent with the anomeric proton of a α-glycosyl tosylate. To further establish the identity of this species, we examined its low-temperature $^1$H—$^{13}$C Heteronuclear Single-Quantum Correlation (HSQC) NMR spectrum. This experiment revealed that the proton at δ 6.11 ppm correlated with a $^{13}$C NMR signal at δ 102.3 ppm, which is consistent with an anomeric carbon (FIG. 3). Together these experiments indicate that the reaction conditions rapidly and essentially quantitatively convert the hemiacetal to the corresponding α-glycosyl tosylate at low temperature. This particular intermediate 2-deoxy glucosyl tosylate persisted for nearly 2 hours at −78° C. without any indication of decomposition or anomerization (FIG. 4A). The tosylate was stable up to temperatures up to −5° C. (FIG. 4B), but it appears to eliminate rapidly to form the corresponding glucal above this threshold (FIG. 4C). The experiments further corroborate our proposed mechanism in which the hemiacetal is converted to an α-glycosyl tosylate that reacts through an $S_N2$-mechanism.

An aspect of the invention is a method of forming a glycosidic bond, the method comprising the steps of:

combining a first solvent, a reducing sugar, and a first strong Bronsted base, thereby forming a first reaction mixture;

combining a sulfonylating agent and the first reaction mixture, thereby forming a glycosyl sulfonate;

combining a second solvent, a glycosyl acceptor, and a second strong Bronsted base, thereby forming a second reaction mixture; and combining the glycosyl sulfonate and the second reaction mixture, thereby forming a glycosidic bond;

wherein the glycosidic bond is formed with greater than or equal to 60% stereoselectivity for a particular stereochemical configuration.

In various individual embodiments, the glycosidic bond is formed with greater than or equal to 70%, 75%, 80%, or 85% stereoselectivity for a particular stereochemical configuration.

In one embodiment, the glycosidic bond is formed with greater than or equal to 90% stereoselectivity for a particular stereochemical configuration.

In various individual embodiments, the glycosidic bond is formed with greater than or equal to 91%, 92%, 93%, or 94% stereoselectivity for a particular stereochemical configuration.

In one embodiment, the glycosidic bond is formed with greater than or equal to 95% stereoselectivity for a particular stereochemical configuration.

In one embodiment, the glycosidic bond is formed with greater than or equal to 96% stereoselectivity for a particular stereochemical configuration.

In one embodiment, the glycosidic bond is formed with greater than or equal to 97% stereoselectivity for a particular stereochemical configuration.

In one embodiment, the glycosidic bond is formed with greater than or equal to 98% stereoselectivity for a particular stereochemical configuration.

In one embodiment, the glycosidic bond is formed with greater than or equal to 99% stereoselectivity for a particular stereochemical configuration.

In each of the foregoing embodiments, the degree of stereoselectivity can be assessed using any suitable method. For example, the degree of stereoselectivity can be assessed by NMR or by measuring optical rotation with a polarimeter.

In one embodiment, the reducing sugar is a 2-deoxy-sugar.

In one embodiment, the reducing sugar is a pyranose.

In one embodiment, the reducing sugar is a furanose.

In one embodiment, the reducing sugar is a D-sugar; and the particular stereochemical configuration is a β linkage.

In one embodiment, the reducing sugar is a 2-deoxy-D-sugar.

In one embodiment, the reducing sugar is a D-pyranose.

In one embodiment, the reducing sugar is a D-furanose.

In one embodiment, the reducing sugar is an L-sugar.

In one embodiment, the reducing sugar is an L-sugar; and the particular stereochemical configuration is a β linkage.

In one embodiment, the reducing sugar is a 2-deoxy-L-sugar.

In one embodiment, the reducing sugar is an L-pyranose.

In one embodiment, the reducing sugar is an L-furanose.

In one embodiment, the reducing sugar is a 2,6-dideoxy-L-sugar.

In one embodiment in accordance with each of the foregoing, the reducing sugar is selected from the group consisting of:

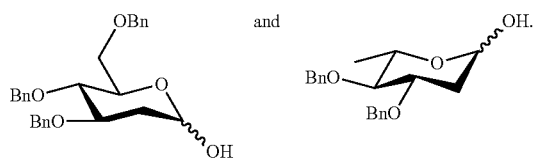

In one embodiment in accordance with each of the foregoing, the first strong Bronsted base is non-nucleophilic.

In one embodiment in accordance with each of the foregoing, the second strong Bronsted base is non-nucleophilic.

In one embodiment in accordance with each of the foregoing, the first strong Bronsted base is non-nucleophilic; and the second strong Bronsted base is non-nucleophilic.

In one embodiment in accordance with each of the foregoing, the first strong Bronsted base is selected from the group consisting of: alkali metal alkoxides, alkali metal amides, alkaline earth metal alkoxides, and alkaline earth metal amides.

In one embodiment in accordance with each of the foregoing, the first strong Bronsted base is selected from the group consisting of: sodium tert-butoxide, potassium tert-butoxide, lithium tert-butoxide, lithium diisopropylamide, lithium tetramethylpiperidide, sodium hexamethyldisilazane (NaHMDS), and potassium hexamethyldisilazane (KHMDS).

In one embodiment in accordance with each of the foregoing, the first strong Bronsted base is KHMDS.

In one embodiment in accordance with each of the foregoing, the second strong Bronsted base is selected from the group consisting of: alkali metal alkoxides, alkali metal amides, alkaline earth metal alkoxides, and alkaline earth metal amides.

In one embodiment in accordance with each of the foregoing, the second strong Bronsted base is selected from the group consisting of: sodium tert-butoxide, potassium tert-butoxide, lithium tert-butoxide, lithium diisopropylamide, lithium tetramethylpiperidide, NaHMDS, and KHMDS.

In one embodiment in accordance with each of the foregoing, the second strong Bronsted base is KHMDS.

In one embodiment in accordance with each of the foregoing, the first strong Bronsted base is same as the second strong Bronsted base.

In one embodiment in accordance with each of the foregoing, the sulfonylating agent is selected from the group consisting of: sulfonic anhydrides, sulfonyl halides, and N-sulfonylimidazoles.

In one embodiment in accordance with each of the foregoing, the sulfonylating agent is selected from the group consisting of: sulfonic anhydrides and N-sulfonylimidazoles.

In one embodiment in accordance with each of the foregoing, the sulfonylating agent is selected from the group consisting of: sulfonic anhydrides.

In one embodiment in accordance with each of the foregoing, the sulfonylating agent is selected from the group consisting of: methanesulfonic anhydride, benzenesulfonic anhydride, and p-toluenesulfonic anhydride.

In one embodiment in accordance with each of the foregoing, the sulfonylating agent is selected from the group consisting of: N-sulfonylimidazoles.

In one embodiment in accordance with each of the foregoing, the sulfonylating agent is selected from the group consisting of: p-toluenesulfonic anhydride and N-sulfonylimidazoles.

In one embodiment in accordance with each of the foregoing, the sulfonylating agent is p-toluenesulfonic anhydride.

In one embodiment in accordance with each of the foregoing, the sulfonylating agent is tosyl-4-nitroimidazole.

In one embodiment in accordance with each of the foregoing, the first reaction mixture further comprises tri-tert-butylpyrimidine (TTBP).

In one embodiment in accordance with each of the foregoing, the glycosyl acceptor comprises an alcohol, a thiol, or an amine.

In one embodiment in accordance with each of the foregoing, the glycosyl acceptor is a monosaccharide, a disaccharide, an oligosaccharide, or a polysaccharide, each comprising at least one —OH, —SH, or primary or secondary amino group.

In one embodiment in accordance with each of the foregoing, the glycosyl acceptor is selected from the group consisting of: PhSH, t-BuSH, 2-naphthol, 1-naphthol, phenol, o-cresol, p-methoxyphenol, p-trifluoromethylphenol,

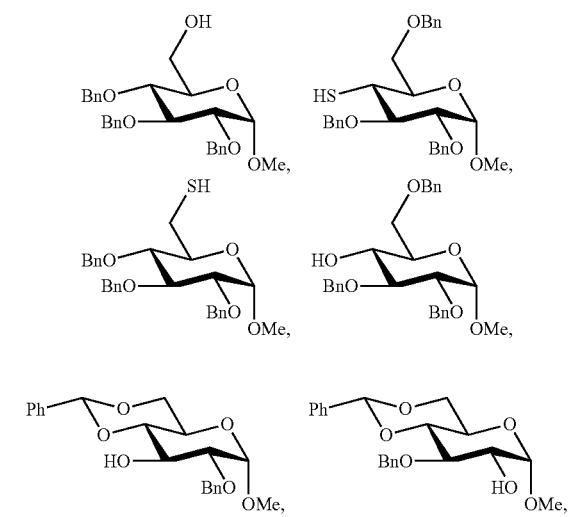

-continued

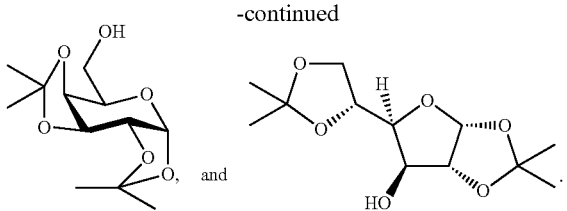

In one embodiment in accordance with each of the foregoing, the first solvent is selected from the group consisting of tetrahydrofuran (THF), diglyme, and a combination of THF and diglyme.

In one embodiment in accordance with each of the foregoing, the first solvent is THF.

In one embodiment in accordance with each of the foregoing, the first solvent is a combination of THF and diglyme.

In one embodiment in accordance with each of the foregoing, the second solvent is selected from the group consisting of THF, diglyme, and a combination of THF and diglyme.

In one embodiment in accordance with each of the foregoing, the second solvent is THF.

In one embodiment in accordance with each of the foregoing, the second solvent is a combination of THF and diglyme.

In one embodiment in accordance with each of the foregoing, the first solvent is the same as the second solvent.

In other embodiments, any of the aforementioned methods of the invention can be performed without the first solvent, the second solvent, or both of them.

Thus, the invention further contemplates a method of forming a glycosidic bond, comprising:
 combining a solvent, a reducing sugar, and a first strong Bronsted base, thereby forming a first reaction mixture;
 combining a sulfonylating agent and the first reaction mixture, thereby forming a glycosyl sulfonate;
 combining a glycosyl acceptor and a second strong Bronsted base, thereby forming a second reaction mixture; and
 combining the glycosyl sulfonate and the second reaction mixture, thereby forming a glycosidic bond;
 wherein the glycosidic bond is formed with greater than or equal to 60% stereoselectivity for a particular stereochemical configuration.

In one embodiment in accordance with the foregoing, the solvent is selected from the group consisting of tetrahydrofuran (THF), diglyme, and a combination of THF and diglyme.

In one embodiment in accordance with the foregoing, the solvent is THF.

In one embodiment in accordance with the foregoing, the solvent is a combination of THF and diglyme.

The invention further contemplates a method of forming a glycosidic bond, comprising:
 combining a reducing sugar and a first strong Bronsted base, thereby forming a first reaction mixture;
 combining a sulfonylating agent and the first reaction mixture, thereby forming a glycosyl sulfonate;
 combining a solvent, a glycosyl acceptor, and a second strong Bronsted base, thereby forming a second reaction mixture; and
 combining the glycosyl sulfonate and the second reaction mixture, thereby forming a glycosidic bond;
 wherein the glycosidic bond is formed with greater than or equal to 60% stereoselectivity for a particular stereochemical configuration.

In one embodiment in accordance with the foregoing, the solvent is selected from the group consisting of tetrahydrofuran (THF), diglyme, and a combination of THF and diglyme.

In one embodiment in accordance with the foregoing, the solvent is THF.

In one embodiment in accordance with the foregoing, the solvent is a combination of THF and diglyme.

Moreover, the invention further contemplates a method of forming a glycosidic bond, comprising:
 combining a reducing sugar and a first strong Bronsted base, thereby forming a first reaction mixture;
 combining a sulfonylating agent and the first reaction mixture, thereby forming a glycosyl sulfonate;
 combining a glycosyl acceptor and a second strong Bronsted base, thereby forming a second reaction mixture; and
 combining the glycosyl sulfonate and the second reaction mixture, thereby forming a glycosidic bond;
 wherein the glycosidic bond is formed with greater than or equal to 60% stereoselectivity for a particular stereochemical configuration.

In yet additional embodiments, the methods of the invention can be carried out in a fluorous phase, in an ionic liquid, or in solid- or polymer-supported synthetic methods.

Any of the aforementioned methods of the invention can be applied in an iterative synthetic procedure, wherein the donor(s) and acceptor(s) possess the same leaving group(s).

EXEMPLIFICATION

The present invention is further illustrated by the following examples, which in no way should be construed as further limiting. The entire contents of all the references (including literature references, issued patents, published patent applications, and co-pending patent applications) cited throughout this application are hereby expressly incorporated by reference.

EXAMPLES

General Experimental Details

All reactions were performed under inert argon atmosphere. Flash column chromatography was performed on SiliCycle P-60 silica gel, 230-400 Mesh. Analytical and preparative thin layer chromatography was carried out on EMD silica gel 60 F-254 plates. Products were visualized using UV or by staining with 5% aqueous sulfuric acid or ceric ammonium molybdate. NMR spectra were recorded on a Bruker Avance III NMR spectrometer at 500 MHz for $^1$H NMR and 125 MHz for $^{13}$C NMR, and 500 MHz for Gradient HSQC. Chemical shifts are reported in ppm relative to tetramethylsilane (TMS) (for $^1$H NMR in CDCl$_3$) or CDCl$_3$ (for $^{13}$C NMR in CDCl$_3$). For $^1$H NMR spectra, data are reported as follows: shift, multiplicity [s=singlet, m=multiplet, t=triplet, d=doublet, dd=doublet of doublets, ddd=doublet of doublet of doublets, dt=doublet of triplets, td=triplet of doublets, q=quartet], coupling constants are reported in Hz. Low resolution mass spectra (LRMS) were obtained using a Finnigan LTQ ESI-MS with an additional APCI source. High resolution mass spectra (HRMS) were obtained at Massachusetts Institute of Technology Department of Chemistry instrumentation facility using a peak-matching protocol to determine the mass and error range of the molecular ion. Optical rotations were measured on a Rudolph Research Analysis AUTOPUL IV polarimeter in a 5 cm cell at 23-24° C., and concentrations are reported in grams per 100 mL, with reference to the sodium D line at 589 nm.

Materials

Prior to running the glycosylation reactions, all donors and acceptors were dried twice by azeotropic removal of water using toluene and a rotary evaporator at <40° C. Solvents for reactions were dried on an Innovative Technologies PureSolv 400 solvent purifier. NMR solvents were purchased from Cambridge Isotope Labs. Compounds 1a, and 17; tosyl 4-nitroimidazole; compounds 4, 5, and 6; glycosyl donors 1a and 1b; and glycosyl acceptors 102a-102d were synthesized according to literature procedures. All other chemicals were purchased at the highest possible purity from Carbosynth, TCI, Alfa Aesar, and Sigma-Aldrich and used as received. The 5 mm Low Pressure/Vacuum Valve NMR tube used for low-temperature NMR experiments was purchased from Wilmad LabGlass.

Example 1

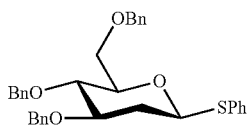

2

Phenyl 3,4,6-tri-O-benzyl-2-deoxy-1-thio-β-D-glucopyranoside (2)

A solution of donor 1a (1.5 equiv., 0.375 mmol, 162.8 mg; see Table 1) in 3.0 mL THF was cooled to −78° C. and treated dropwise with potassium hexamethyldisilazane (1 M in THF, 1.5 equiv, 0.375 mmol, 0.375 mL). After 15 minutes, a solution of tosyl 4-nitroimidazole (1.5 equiv., 0.375 mmol, 100.2 mg) in 2.0 mL THF was added rapidly to the reaction. The solution was maintained at −78° C. for 1 h, and then treated with thiophenol (1.0 equiv, 0.250 mmol, 25.6 μL). The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (10% ethyl acetate in hexanes) to afford product 2 as a single β-anomer (0.220 mmol, 115.8 mg, 88% yield).

$^1$H NMR (500 MHz, CDCl$_3$): δ 7.55-7.48 (m, 2H), 7.39-7.18 (m, 18H), 4.92-4.86 (d, J=11.0 Hz, 1H), 4.77-4.72 (d, J=11.5 Hz, 1H), 4.70-4.65 (d, J=11.5 Hz, 1H), 4.63-4.51 (m, 4H), 3.83-3.76 (m, 1H), 3.75-3.72 (d, J=5.0 Hz, 1H), 3.72-3.65 (m, 1H), 3.55 (m, 2H), 2.44 (dd, J=12.0, 4.0 Hz, 1H), 1.81 (q, J=12.0 Hz, 1H).

$^{13}$C NMR (125 MHz, CDCl$_3$): δ 138.5, 138.5, 138.3, 134.2, 131.5, 128.9, 128.6, 128.5, 128.4, 128.1, 127.8, 127.8, 127.8, 127.6, 127.4, 82.2, 80.8, 79.5, 78.0, 75.2, 73.5, 71.8, 69.6, 37.0.

LRMS (ESI, pos. ion) m/z: calculated for C$_{33}$H$_{34}$O$_4$S [M+Na] 549.21. found 549.27.

HRMS (ESI, pos. ion) m/z: calculated for C$_{33}$H$_{34}$O$_4$S [M+Na] 549.2070. found 549.2072.

[α]$^{24}_D$=−32.2 (c 1.00, CH$_2$Cl$_2$).

Example 2

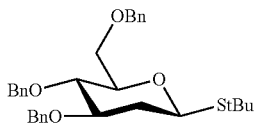

7 tert-Butyl 3,4,6-tri-O-benzyl-2-deoxy-1-thio-β-D-glucopyranoside (7)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF was added rapidly to the reaction. The solution was maintained at −78° C. for 1 h. Thiol acceptor 3, tert-butyl mercaptan (1.0 equiv., 0.250 mmol, 28.2 μL), was dissolved in 1.0 mL THF, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (5% ethyl acetate in hexanes) to afford product 7 as a single β-anomer (0.103 mmol, 51.9 mg, 41% yield).

$^1$H NMR (500 MHz, CDCl$_3$): δ 7.36-7.21 (m, 15H), 4.93-4.87 (d, J=11.0 Hz, 1H), 4.71-4.65 (m, 2H), 4.62-4.51 (m, 4H), 3.77-3.63 (m, 3H), 3.48-3.42 (m, 2H), 2.33 (ddd, J=12.5, 5.5, 1.5 Hz, 1H), 1.75 (q, J=11.5 Hz, 1H).

$^{13}$C NMR (125 MHz, CDCl$_3$): δ 138.6, 138.5, 128.6, 128.5, 128.4, 128.1, 127.8, 127.7, 127.5, 81.1, 79.1, 78.3, 78.2, 75.1, 73.5, 71.6, 70.0, 44.1, 37.4, 31.8.

LRMS (ESI, pos. ion) m/z: calculated for C$_{31}$H$_{38}$O$_{45}$ [M+Na] 529.24. found 529.36.

HRMS (ESI, pos. ion) m/z: calculated for C$_{31}$H$_{38}$O$_{45}$ [M+Na] 529.2383. found 529.2382. [α]$^{24}_D$=−28.8 (c 0.75, CH$_2$Cl$_2$).

Example 3

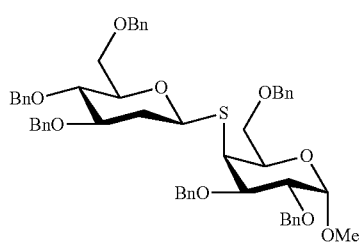

8

Methyl (3,4,6-tri-O-benzyl-2-deoxy-β-D-glucopyranosyl)-(1→4)-2,3,6-tri-O-benzyl-4-deoxy-4-thio-α-D-galactopyranoside (8)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF was added rapidly to the reaction. The solution was maintained at −78° C. for 1 h. Thiol acceptor 4 (1.0 equiv., 0.250 mmol, 120.2 mg) was dissolved in 2.0 mL THF, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (20% ethyl acetate in hexanes) to afford product 8 as a single β-anomer (0.200 mmol, 179.4 mg, 80% yield).

$^1$H NMR (500 MHz, $CDCl_3$): δ 7.39-7.35 (m, 2H), 7.34-7.17 (m, 28H), 4.89-4.78 (m, 3H), 4.71 (d, J=11.0 Hz, 1H), 4.67-4.59 (m, 4H), 4.57-4.49 (m, 5H), 4.44 (d, J=12.0 Hz, 1H), 4.22-4.17 (m, 1H), 4.06 (dd, J=10.0, 4.0 Hz, 1H), 3.97 (dd, J=9.5, 3.5 Hz, 1H), 3.80-3.71 (m, 2H), 3.70-3.58 (m, 3H), 3.50-3.43 (m, 2H), 3.36 (s, 3H), 3.31-3.25 (m, 1H), 2.39 (dd, J=13.0, 2.0 Hz, 1H), 1.65-1.55 (m, 1H).

$^{13}$C NMR (125 MHz, $CDCl_3$) δ 138.7, 138.6, 138.5, 138.4, 138.4, 138.4, 128.5, 128.5, 128.4, 128.4, 128.3, 128.1, 128.0, 127.8, 127.7, 127.7, 127.6, 127.6, 127.5, 127.5, 127.4, 98.6, 80.8, 79.6, 79.2, 78.6, 78.0, 77.7, 77.4, 77.2, 76.9, 75.0, 73.6, 73.5, 73.4, 73.2, 72.1, 71.4, 69.7, 69.7, 55.2, 48.0, 37.0.

LRMS (ESI, pos. ion) m/z: calculated for $C_{55}H_{60}O_9S$ [M+Na] 919.39. found 919.41.

HRMS (ESI, pos. ion) m/z: calculated for $C_{55}H_{60}O_9S$ [M+Na] 919.3850. found 919.3840.

$[\alpha]^{24}_D$=+13.6 (c 1.00, $CH_2Cl_2$).

Example 4

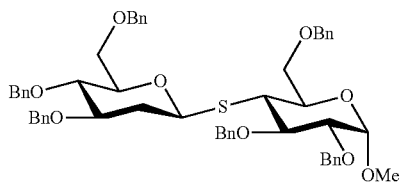

Methyl (3,4,6-tri-O-benzyl-2-deoxy-β-D-glucopyranosyl)-(1→4)-2,3,6-tri-O-benzyl-4-deoxy-4-thio-α-D-glucopyranoside (9)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL of THF was added rapidly to the reaction. The solution was maintained at −78° C. for 1 h. Thiol acceptor 5 (1.0 equiv., 0.250 mmol, 120.2 mg) was dissolved in 2.0 mL THF, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (10% ethyl acetate in hexanes) to afford product 9 as a single β-anomer (0.113 mmol, 100.8 mg, 45% yield).

$^1$H NMR (500 MHz, $CDCl_3$): δ 7.45-7.41 (m, 2H), 7.35-7.16 (m, 28H), 4.92 (d, J=10.5 Hz, 1H), 4.85 (d, J=7.5 Hz, 1H), 4.83 (d, J=7.0 Hz, 1H), 4.77 (d, J=12.0 Hz, 1H), 4.65 (d, J=3.5 Hz, 1H), 4.63 (d, J=12.0 Hz, 1H), 4.58-4.51 (m, 4H), 4.51-4.46 (m, 2H), 4.51-4.39 (m, 2H), 4.04-3.94 (m, 2H), 3.85 (dd, J=10.5, 9.5 Hz, 1H), 3.77 (d, J=9.5 Hz, 1H), 3.60-3.54 (m, 3H), 3.52-3.41 (m, 2H), 3.30-3.24 (m, 1H), 3.27 (s, 3H), 3.05 (t, J=10.5 Hz, 1H), 2.12 (ddd, J=12.5, 5.0, 1.5 Hz, 1H), 1.72 (q, J=12 Hz, 1H).

$^{13}$C NMR (125 MHz, $CDCl_3$): δ 138.7, 138.4, 138.4, 138.3, 138.3, 138.1, 128.4, 128.4, 128.3, 128.3, 128.2, 128.2, 128.2, 128.1, 127.9, 127.9, 127.7, 127.6, 127.6, 127.5, 127.5, 127.4, 98.1, 81.3, 80.7, 79.1, 77.9, 77.6, 77.3, 75.7, 74.9, 73.4, 73.2, 71.4, 70.7, 69.7, 69.4, 55.0, 46.5, 37.4.

LRMS (ESI, pos. ion) m/z: calculated for $C_{55}H_{60}O_9S$ [M+Na] 919.39. found 919.36.

HRMS (ESI, pos. ion) m/z: calculated for $C_{55}H_{60}O_9S$ [M+Na] 919.3850. found 919.3858.

$[\alpha]^{24}_D$=+6.8 (c 1.00, $CH_2Cl_2$).

Example 5

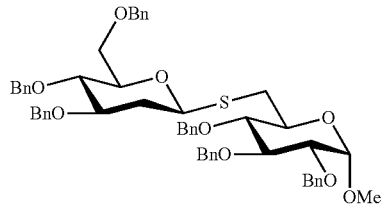

Methyl (3,4,6-tri-O-benzyl-2-deoxy-β-D-glucopyranosyl)-(1→6)-2,3,4-tri-O-benzyl-6-deoxy-6-thio-α-D-glucopyranoside (10)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL of THF was added rapidly to the reaction. The solution was maintained at −78° C. for 1 h. Thiol acceptor 6 (1.0 equiv., 0.250 mmol, 120.2 mg) was dissolved in 2.0 mL THF, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (10% ethyl acetate in hexanes) to afford product 10 as a single β-anomer (0.125 mmol, 112.1 mg, 50% yield).

$^1$H NMR (500 MHz, $CDCl_3$): δ 7.43-7.22 (m, 30H), 4.97 (d, J=11.0 Hz, 1H), 4.87 (d, J=11.0 Hz, 1H), 4.87 (d, J=11.5 Hz, 1H), 4.80-4.75 (m, 2H), 4.66 (d, J=8.0 Hz, 1H), 4.64 (d, J=8.0 Hz, 1H), 4.61-4.53 (m, 5H), 4.50 (d, J=12.0 Hz, 1H), 4.46 (dd, J=11.5, 1.5 Hz, 1H), 3.95 (t, J=9.0 Hz, 1H), 3.83 (dt, J=9.0, 2.5 Hz, 1H), 3.73-3.66 (m, 2H), 3.64-3.57 (m, 1H), 3.53-3.47 (m, 2H), 3.37 (s, 3H), 3.36-3.33 (m, 1H), 3.29 (t, J=9.0 Hz, 1H), 3.09 (dd, J=13.5, 2.5 Hz, 1H), 2.68 (dd, J=13.5, 9.0 Hz, 1H), 2.30 (ddd, J=12.5, 5.0, 1.5 Hz, 1H), 1.68 (q, J=12.0 Hz, 1H).

$^{13}$C NMR (125 MHz, $CDCl_3$): δ 138.9, 128.5, 128.4, 128.2, 128.1, 128.1, 81.1, 80.8, 80.7, 80.2, 79.5, 78.1, 75.8, 75.2, 75.1, 73.5, 73.4, 71.6, 71.1, 69.6, 55.3, 37.3, 32.7.

LRMS (ESI, pos. ion) m/z: calculated for $C_{55}H_{60}O_9S$ [M+Na] 919.39. found 919.27.

HRMS (ESI, pos. ion) m/z: calculated for $C_{55}H_{60}O_9S$ [M+Na] 919.3850. found 919.3830.

$[α]^{24}_D$=+19.0 (c 1.00, $CH_2Cl_2$).

Example 6

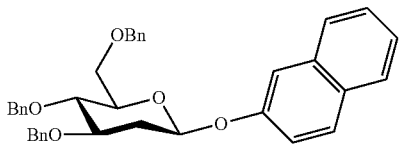

11

2-Naphthyl 3,4,6-tri-O-benzyl-2-deoxy-β-D-glucopyranoside (11)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL of THF and 2.0 mL diglyme was added rapidly to the reaction. The solution was maintained at −78° C. for 1 h. 2-Naphthol (1.0 equiv., 0.250 mmol, 36.0 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (10% ethyl acetate in hexanes) to afford product 11 as a single β-anomer (0.190 mmol, 106.5 mg, 76% yield).

$^1$H NMR (500 MHz, $CDCl_3$): δ 7.73 (d, J=8.0 Hz, 1H), 7.71 (d, J=9.0 Hz, 1H), 7.61 (d, J=8.0 Hz, 1H), 7.41-7.18 (m, 19H), 5.17 (dd, J=9.5, 2.0 Hz, 1H), 4.93 (d, J=11.0 Hz, 1H), 4.70 (d, J=12.0 Hz, 1H), 4.64-4.55 (m, 3H), 4.52 (d, J=12.0 Hz, 1H), 3.85 (dd, J=11.0, 1.5 Hz, 1H), 3.79-3.70 (m, 2H), 3.67-3.62 (m, 1H), 3.61-3.56 (m, 1H), 2.54 (ddd, J=12.5, 5.0, 2.0 Hz, 1H), 2.00 (dt, J=12.0, 10.5 Hz, 1H).

$^{13}$C NMR (125 MHz, $CDCl_3$): δ 155.0, 138.4, 138.4, 138.3, 134.5, 129.8, 129.4, 128.6, 128.5, 128.4, 128.1, 127.8, 127.8, 127.8, 127.7, 127.6, 127.4, 126.4, 124.3, 119.1, 111.0, 97.9, 79.3, 78.1, 77.4, 77.2, 76.9, 75.6, 75.0, 73.6, 71.7, 69.5, 36.6.

LRMS (ESI, pos. ion) m/z: calculated for $C_{37}H_{36}O_5$ [M+Na] 583.25. found 583.36.

HRMS (ESI, pos. ion) m/z: calculated for $C_{37}H_{36}O_5$ [M+Na] 583.2455. found 583.2463.

$[α]^{24}_D$=−51.4 (c 1.00, $CH_2Cl_2$).

Example 7

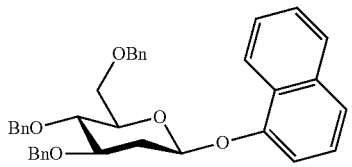

12

1-Naphthyl 3,4,6-tri-O-benzyl-2-deoxy-β-D-glucopyranoside (12)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL of THF and 2.0 mL diglyme was added rapidly to the reaction. The solution was maintained at −78° C. for 1 h. 1-Naphthol (1.0 equiv., 0.250 mmol, 36.0 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (1% diethyl ether in toluene) to afford product 12 as a single β-anomer (0.175 mmol, 98.1 mg, 70% yield).

$^1$H NMR (500 MHz, $CDCl_3$): δ 8.27-8.21 (m, 1H), 7.81-7.76 (m, 1H), 7.51-7.42 (m, 3H), 7.39-720 (m, 16H), 7.12 (d, J=8.0 Hz, 1H), 5.23 (dd, 9.5, 2.0 Hz, 1H), 4.94 (d, J=11.0 Hz, 1H), 4.74 (d, J=11.5 Hz, 1H), 4.65 (d, J=12.0 Hz, 1H), 4.63-4.50 (m, 3H), 3.87-3.82 (m, 1H), 3.82-3.71 (m, 2H), 3.68-3.61 (m, 2H), 2.64 (ddd, J=12.0, 4.5, 2.0 Hz, 1H), 2.15 (td, J=12.0, 10.0 Hz, 1H).

$^{13}$C NMR (125 MHz, CDCl$_3$): δ 153.1, 138.5, 138.4, 138.4, 134.6, 128.6, 128.5, 128.4, 128.1, 127.9, 127.9, 127.8, 127.6, 127.6, 126.4, 126.0, 126.0, 125.5, 122.2, 122.1, 109.1, 98.3, 79.3, 78.0, 77.4, 77.2, 76.9, 75.7, 75.1, 73.6, 71.8, 69.4, 36.7.

LRMS (ESI, pos. ion) m/z: calculated for C$_{37}$H$_{36}$O$_5$ [M+Na] 583.25. found 583.36.

HRMS (ESI, pos. ion) m/z: calculated for C$_{37}$H$_{36}$O$_5$ [M+Na] 583.2455. found 583.2463.

$[α]^{24}_D$=−41.4 (c 1.00, CH$_2$Cl$_2$).

Example 8

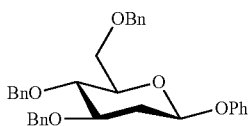

13

Phenyl 3,4,6-tri-O-benzyl-2-deoxy-β-D-glucopyranoside (13)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. Phenol (1.0 equiv., 0.250 mmol, 23.5 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (5% ethyl acetate in toluene) to afford product 13 as a single β-anomer (0.168 mmol, 85.5 mg, 67% yield).

$^1$H NMR (500 MHz, C$_6$D$_6$): δ 7.37-7.19 (m, 17H), 7.03 (d, J=8.0 Hz, 2H), 7.00 (t, J=7.5 Hz, 1H), 5.06 (dd, J=9.5, 2.0 Hz, 1H), 4.92 (d, J=10.5, 1H), 4.70 (d, J=11.5, 1H), 4.63 (d, J=11.5, 1H), 4.60-4.56 (m, 2H), 4.53 (d, J=12.0 Hz, 1H), 3.84-3.79 (m, 1H), 3.77-3.69 (m, 1H), 3.61-3.55 (m, 1H), 2.50 (ddd, J=12.5, 5.0, 2.0 Hz, 1H), 1.95 (dt, J=12.0, 10.0 Hz, 1H).

$^{13}$C NMR (125 MHz, CDCl$_3$): δ 157.3, 138.5, 138.4, 138.3, 129.5, 128.6, 128.5, 128.4, 128.1, 127.8, 127.8, 127.8, 127.6, 122.4, 116.7, 97.8, 79.3, 78.0, 77.4, 77.2, 76.9, 75.6, 75.1, 73.6, 71.7, 69.4, 36.7.

LRMS (ESI, pos. ion) m/z: calculated for C$_{33}$H$_{34}$O$_5$ [M+Na] 533.23. found 533.36.

HRMS (ESI, pos. ion) m/z: calculated for C$_{33}$H$_{34}$O$_5$ [M+Na] 533.2298. found 533.2319.

$[α]^{24}_D$=−29.6 (c 1.00, CH$_2$Cl$_2$).

Example 9

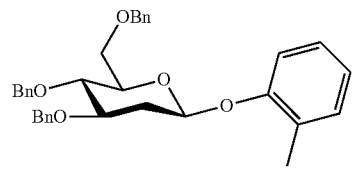

14 o-Cresyl 3,4,6-tri-O-benzyl-2-deoxy-β-D-glucopyranoside (14)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. 0-Cresol (1.0 equiv., 0.250 mmol, 25.7 μL) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (1% diethyl ether in toluene) to afford product 14 as a single β-anomer (0.155 mmol, 81.3 mg, 62% yield).

$^1$H NMR (500 MHz, CDCl$_3$): δ 7.38-7.21 (m, 15H), 7.14-7.03 (m, 3H), 6.91 (dt, J=7.5, 1.0 Hz, 1H), 5.02 (dd, J=9.5, 2.0 Hz, 1H), 4.92 (d, J=11.0 Hz, 1H), 4.72 (d, J=11.5 Hz, 1H), 4.63 (d, J=11.5 Hz, 1H), 4.61-4.56 (m, 2H), 4.53 (d, J=12.0 Hz, 1H), 3.81 (dd, J=10.5, 1.5 Hz, 1H), 3.78-3.69 (m, 2H), 3.63-3.53 (m, 2H), 2.52 (ddd, J=12.0, 4.5, 1.5 Hz, 1H), 2.53 (s, 3H), 2.00 (dt, J=12.0, 10.0 Hz, 1H).

$^{13}$C NMR (125 MHz, CDCl$_3$): δ 155.6, 138.5, 138.4, 138.4, 130.8, 128.6, 128.5, 128.4, 128.1, 127.8, 127.6, 127.6, 127.0, 122.2, 114.9, 98.2, 79.4, 78.1, 77.4, 77.2, 76.9, 75.5, 75.1, 73.6, 71.7, 69.4, 36.8, 16.4.

LRMS (ESI, pos. ion) m/z: calculated for C$_{33}$H$_{34}$O$_5$ [M+Na] 547.25. found 547.36.

HRMS (ESI, pos. ion) m/z: calculated for C$_{33}$H$_{34}$O$_5$ [M+Na] 547.2455. found 547.2456.

$[α]^{24}_D$=−28.6 (c 1.00, CH$_2$Cl$_2$).

Example 10

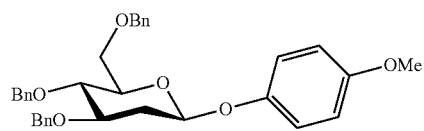

15 p-Methoxyphenyl 3,4,6-tri-O-benzyl-2-deoxy-β-D-glucopyranoside (15)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. 4-methoxyphenol (1.0 equiv., 0.250 mmol, 31.0 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (10% ethyl acetate in hexanes) to afford product 15 as a single β-anomer (0.185 mmol, 100.0 mg, 74% yield).

$^1$H NMR (500 MHz, $CDCl_3$): δ 7.38-7.16 (m, 15H), 6.98 (d, J=9.5 Hz, 2H), 6.77 (d, J=9.0 Hz, 2H), 4.94 (dd, J=9.5, 1.5 Hz, 1H), 4.91 (d, J=11, 0 Hz, 1H), 4.70 (d, J=11.5 Hz, 1H), 4.61 (d, J=11.5 Hz, 1H), 4.60-4.50 (m, 3H), 3.83-3.78 (m, 1H), 3.76-3.68 (m, 5H), 3.59-3.50 (m, 2H), 2.49 (ddd, J=12.5, 5.0, 1.5 Hz, 1H), 1.91. (dt, J=12.0, 10.0 Hz, 1H).

$^{13}$C NMR (125 MHz, $CDCl_3$): δ 155.1, 151.4, 138.5, 138.5, 138.4, 128.6, 128.5, 128.4, 128.1, 127.8, 127.8, 127.6, 118.2, 114.6, 98.8, 79.4, 78.1, 77.4, 77.2, 76.9, 75.5, 75.1, 73.5, 71.7, 69.5, 55.7, 36.8.

LRMS (ESI, pos. ion) m/z: calculated for $C_{34}H_{36}O_6$ [M+Na] 563.24. found 563.64.

HRMS (ESI, pos. ion) m/z: calculated for $C_{34}H_{36}O_6$ [M+Na] 563.2404. found 563.2413.

$[\alpha]^{24}_D$=−20.8 (c 1.00, $CH_2Cl_2$).

Example 11

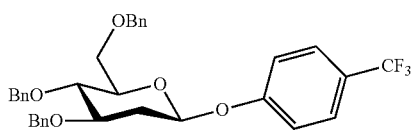

p-Trifluoromethylphenyl 3,4,6-tri-O-benzyl-2-deoxy-β-D-glucopyranoside (16)

A solution of donor 1a (1.5 equiv., 0.375 mmol, 162.8 mg) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. 4-trifluoromethylphenol (1.0 equiv., 0.250 mmol, 40.5 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (10% ethyl acetate in hexanes) to afford product 16 as a single β-anomer (0.113 mmol, 65.0 mg, 45% yield).

$^1$H NMR (500 MHz, $CDCl_3$): δ 7.52-7.47 (d, J=9.0 Hz, 2H), 7.38-7.21 (m, 15H), 7.10-7.05 (d, J=8.5 Hz, 2H), 5.11 (d, J=10.0, 2.0 Hz, 1H), 4.92 (d, J=11.0 Hz, 1H), 4.72 (d, J=12.0 Hz, 1H), 4.64 (d, J=12.0 Hz, 1H), 4.59 (d, J=10.5 Hz, 1H), 4.57 (d, J=12.0 Hz, 1H), 4.50 (d, J=12.0 Hz, 1H), 3.81 (d, J=10.5 Hz, 1H), 3.79-3.73 (m, 1H), 3.72-3.67 (m, 1H), 3.62-3.56 (m, 1H), 2.52 (ddd, J=12.5, 5.0, 2.0 Hz, 1H), 1.97 (td, J=12.0, 10.0 Hz, 1H).

$^{13}$C NMR (125 MHz, $CDCl_3$): δ 159.9, 138.3, 138.3, 138.3, 128.6, 128.5, 128.5, 128.1, 127.9, 127.9, 127.9, 127.8, 127.8, 124.5 (q, $J_{C-F}$=269.9 Hz), 124.4 (q, $J_{C-F}$=32.5 Hz), 116.6, 97.3, 79.1, 77.9, 77.4, 77.2, 76.9, 75.7, 75.1, 73.6, 71.8, 69.3, 36.4.

LRMS (ESI, pos. ion) m/z: calculated for $C_{34}H_{33}F_3O_5$ [M+Na] 601.22. found 601.36.

HRMS (ESI, pos. ion) m/z: calculated for $C_{34}H_{33}F_3O_5$ [M+Na] 601.2172. found 601.2195.

$[\alpha]^{24}_D$=−30.8 (c 1.00, $CH_2Cl_2$).

Example 12

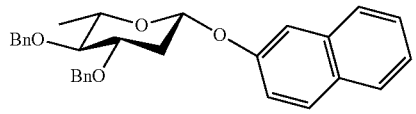

2-Naphthyl 3,4-di-O-benzyl-2,6-dideoxy-β-L-arabino hexopyranoside (18)

A solution of donor 1b (1.5 equiv., 0.375 mmol, 123.2 mg; see Table 4) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. 2-Naphthol (1.0 equiv., 0.250 mmol, 36.0 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and ×15 mL) and then dried ($Na_2SO_4$), filtered, and concentrated under reduced pressure. The crude product was purified by silica gel flash column chromatography (10% ethyl acetate in hexanes) to afford product 18 as a single β-anomer (0.103 mmol, 46.6 mg, 41% yield).

$^1$H NMR (500 MHz, CDCl$_3$): δ 7.77-7.71 (m, 3H), 7.44-7.40 (m, 1H), 7.38-7.27 (m, 12H), 7.19 (dd, J=9.0, 2.5 Hz, 1H), 5.21 (dd, J=10.0, 2.0 Hz, 1H), 4.98 (d, J=11.0 Hz, 1H), 4.74-4.68 (m, 2H), 4.65 (d, J=12.0 Hz, 1H), 3.77-3.71 (m, 1H), 3.60-3.53 (m, 1H), 325 (t, J=8.5 Hz, 1H), 2.55 (ddd, J=12.5, 10.0, 2.0 Hz, 1H), 1.97 (td, J=12.0, 10.0 Hz, 1H), 1.4 (d, J=6.0 Hz, 3H).

$^{13}$C NMR (125 MHz, CDCl$_3$): δ 6 155.0, 1386, 138.4, 134.5, 129.9, 129.5, 128.6, 128.6, 128.2, 127.9, 127.8, 127.3, 126.5, 124.3, 119.0, 110.8, 97.6, 83.6, 79.2, 75.4, 71.9, 71.7, 37.0, 18.5.

LRMS (ESI, pos. ion) m/z: calculated for C$_{30}$H$_{30}$O$_4$ [M+Na] 477.20. found 477.36.

HRMS (DART, pos. ion) m/z: calculated for C$_{30}$H$_{30}$O$_4$ [M+NH$_4$] 472.2482. found 472.2493.

[α]$^{24}_D$=+34.0 (c 1.00, CH$_2$Cl$_2$).

Example 13

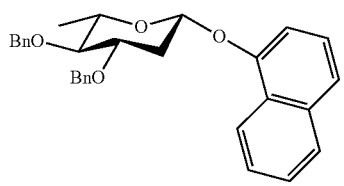

1-Naphthyl 3,4-di-O-benzyl-2,6-dideoxy-β-L-arabino hexopyranoside (19)

A solution of donor 1b (1.5 equiv., 0.375 mmol, 123.2 mg; see Table 4) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. 1-Naphthol (1.0 equiv., 0.250 mmol, 36.0 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (5% ethyl acetate in hexanes) to afford product 19 as a single β-anomer (0.133 mmol, 60.2 mg, 53% yield).

$^1$H NMR (500 MHz, CDCl$_3$): δ 8.26-8.21 (m, 1H), 7.80-7.76 (m, 1H), 7.51-7.43 (m, 3H), 7.40-7.26 (m, 11H), 7.04 (d, J=7.5 Hz, 1H), 5.22 (dd, J=8.5, 1.5 Hz, 1H), 4.99 (d, J=11.0 Hz, 1H), 4.74 (d, J=11.5, 1H), 4.70 (d, J=11.0 Hz, 1H), 4.65 (d, J=12.0 Hz, 1H), 3.78-3.70 (m, 1H), 3.58-3.52 (m, 1H), 3.28 (t, J=9.0 Hz, 1H), 2.63 (ddd, J=12.5, 10.0, 2.0 Hz, 1H), 2.10 (td, J=12.0, 10.0 Hz, 1H), 1.40 (d, J=6.5 Hz, 3H).

$^{13}$C NMR (125 MHz, CDCl$_3$): δ 153.1, 138.6, 138.4, 134.6, 128.6, 128.6, 128.2, 127.9, 127.9, 127.6, 126.5, 126.0, 125.9, 125.5, 122.2, 122.1, 108.7, 98.0, 83.6, 79.2, 75.5, 71.9, 71.7, 37.0, 18.5.

LRMS (ESI, pos. ion) m/z: calculated for C$_{30}$H$_{30}$O$_4$ [M+Na] 477.20. found 477.36.

HRMS (DART, pos. ion) m/z: calculated for C$_{30}$H$_{30}$O$_4$ [M+NH$_4$] 472.2482. found 472.2482.

[α]$^{24}_D$=+64.0 (c 1.00, CH$_2$Cl$_2$).

Example 14

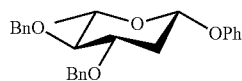

Phenyl 3,4-di-O-benzyl-2,6-dideoxy-β-L-arabino hexopyranoside (20)

A solution of donor 1b (1.5 equiv., 0.375 mmol, 123.2 mg; see Table 4) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. Phenol (1.0 equiv., 0.250 mmol, 23.5 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (5% ethyl acetate in hexanes) to afford product 20 as a single β-anomer (0.183 mmol, 73.8 mg, 73% yield).

$^1$H NMR (500 MHz, CDCl$_3$): δ 7.40-7.23 (m, 12H), 7.02-6.96 (m, 3H), 5.06 (dd, J=10.0, 2.0 Hz, 1H), 4.97 (d, J=11.0 Hz, 1H), 4.71 (d, J=12.0 Hz, 1H), 4.68 (d, J=11.0 Hz, 1H), 4.63 (d, J=11.5 Hz, 1H), 3.74-3.66 (m, 1H), 3.52-3.45 (m, 1H), 3.22 (t, 1=9.0 Hz, 1H), 2.5 (ddd, J=12.0, 4.5, 1.5 Hz, 1H), 1.91 (td, J=12.0, 10.0 Hz, 1H), 1.37 (d, J=6.0 Hz, 3H).

$^{13}$C NMR (125 MHz, CDCl$_3$): δ 15.72, 138.5, 138.4, 129.5, 128.6, 128.5, 128.2, 127.9, 127.9, 122.4, 166.5, 97.4, 83.5, 79.1, 75.4, 71.7, 71.6, 36.9, 18.4.

LRMS (ESI, pos. ion) m/z: calculated for C$_{26}$H$_{28}$O$_4$ [M+Na] 427.219. found 427.27.

HRMS (DART, pos. ion) m/z: calculated for C$_{26}$H$_{28}$O$_4$ [M+NH$_4$] 422.2326. found 422.2336.

[α]$^{24}$D+35.0 (c 1.00, CH$_2$Cl$_2$).

Example 15

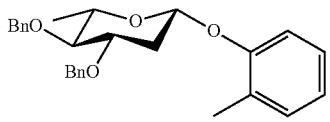

o-Cresyl 3,4-di-O-benzyl-2,6-dideoxy-β-L-arabino hexopyranoside (21)

A solution of donor 1b (1.5 equiv., 0.375 mmol, 123.2 mg; see Table 4) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. O-Cresol (1.0 equiv., 0.250 mmol, 27.0 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (5% ethyl acetate in hexanes) to afford product 21 as a single β-anomer (0.140 mmol, 58.6 mg, 56% yield).

$^1$H NMR (500 MHz, $CDCl_3$): δ 7.38-7.26 (m, 10H), 7.14-7.09 (m, 2H), 6.99-6.95 (m, 1H), 6.93-6.88 (m, 1H), 5.02 (d, J=9.5, 2.0 Hz, 1H), 4.97 (d, J=11.0 Hz, 1H), 4.72 (d, J=11.5 Hz, 1H), 4.68 (d, J=10.5 Hz, 1H), 4.63 (d, J=11.5 Hz, 1H), 3.74-3.67 (m, 1H), 3.52-3.45 (m, 1H), 3.23 (t, J=4.0 Hz, 1H), 2.56 (ddd, J=12.5, 5.0, 2.0 Hz, 1H), 2.23 (s, 3H), 1.96 (td, J=12.0, 10.0 Hz, 1H), 1.37 (d, J=6.5 Hz, 3H).

$^{13}$C NMR (125 MHz, $CDCl_3$): δ 155.6, 138.6, 138.4, 130.9, 128.6, 128.5, 128.2, 127.9, 127.9, 127.7, 126.9, 122.2, 114.5, 97.9, 83.6, 79.2, 75.4, 71.7, 37.0, 18.4, 16.4.

LRMS (ESI, pos. ion) m/z: calculated for $C_{27}H_{30}O_4$ [M+Na] 441.20. found 441.45.

HRMS (DART, pos. ion) m/z: calculated for $C_{27}H_{30}O_4$ [M+NH$_4$] 436.2482. found 436.2493.

$[α]^{24}_D$=+19.2 (c 1.00, $CH_2Cl_2$).

Example 16

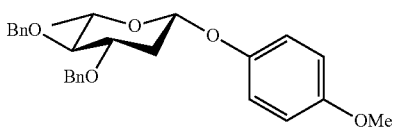

p-Methoxyphenyl 3,4-di-O-benzyl-2,6-dideoxy-β-L-arabino hexopyranoside (22)

A solution of donor 1b (1.5 equiv., 0.375 mmol, 123.2 mg; see Table 4) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. 4-methoxyphenol (1.0 equiv., 0.250 mmol, 31.0 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (5% ethyl acetate in hexanes) to afford product 22 as a single β-anomer (0.158 mmol, 68.4 mg, 63% yield).

$^1$H NMR (500 MHz, $CDCl_3$): δ 7.37-7.25 (m, 10H), 6.97-6.92 (m, 2H), 6.82-6.78 (m, 2H), 4.98-4.92 (m, 2H), 4.70 (d, J=12.0 Hz, 1H), 4.67 (d, J=11.0 Hz, 1H), 4.62 (d, J=11.5 Hz, 1H), 3.74 (s, 3H), 3.71-3.65 (m, 1H), 3.47-3.41 (m, 1H), 3.21 (t, J=9.0 Hz, 1H), 2.49 (ddd, J=12.5, 5.0, 2.0 Hz, 1H), 1.87 (td, J=, 12.5, 10.0 Hz, 1H), 1.36 (d, J=6.0 Hz, 3H).

$^{13}$C NMR (125 MHz, $CDCl_3$): δ 155.2, 151.3, 138.6, 138.4, 128.6, 128.5, 128.2, 127.9, 127.8, 118.0, 114.6, 98.5, 83.6, 79.2, 75.4, 71.6, 55.7, 37.0, 18.4.

LRMS (ESI, pos. ion) m/z: calculated for $C_{27}H_{30}O_5$ [M+Na] 457.20. found 457.36.

HRMS (DART, pos. ion) m/z: calculated for $C_{27}H_{30}O_5$ [M+NH$_4$] 452.2431. found 452.2438.

$[α]^{24}_D$=+16.8 (c 1.00, $CH_2Cl_2$).

Example 17

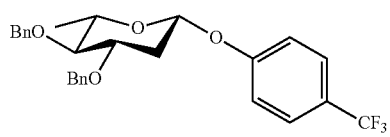

p-Trifluoromethylphenyl 3,4-di-O-benzyl-2,6-dideoxy-β-L-arabino hexopyranoside (23)

A solution of donor 1b (1.5 equiv., 0.375 mmol, 123.2 mg; see Table 4) in 3.0 mL THF was cooled to −78° C. and treated dropwise with potassium hexamethyldisilazane (1 M in THF, 1.5 equiv., 0.375 mmol, 0.375 mL). After 15 minutes, a solution of tosyl 4-nitroimidazole (1.5 equiv., 0.375 mmol, 100.2 mg) in 2.0 mL THF and 2.0 mL diglyme was added rapidly to the reaction. The solution was maintained at −78° C. for 1 h. 4-trifluoromethylphenol (1.0 equiv., 0.250 mmol, 40.5 mg) was dissolved in 1.0 mL THF and 1.0 mL diglyme, cooled to −78° C., and treated with potassium hexamethyldisilazane (1.0 equiv., 0.250 mmol, 0.250 mL). After 15 minutes, this solution was transferred dropwise to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (5% ethyl acetate in hexanes) to afford product 23 as a single β-anomer (0.178 mmol, 83.9 mg, 71% yield).

$^1$H NMR (500 MHz, CDCl$_3$): δ 7.52 (d, J=9.0 Hz, 2H), 7.38-7.26 (m, 10H), 7.02 (d, J=8.5 Hz, 2H), 5.10 (dd, J=10.0, 2.0 Hz, 1H), 4.97 (d, J=11.0 Hz, 1H), 4.71 (d, J=12, 0 Hz, 1H), 4.68 (d, J=11.0 Hz, 1H), 4.64 (d, J=12.0 Hz, 1H), 3.74-3.68 (m, 1H), 3.54-3.47 (m, 1H), 3.23 (t, J=9.0 Hz, 1H), 2.50 (ddd, J=12.5, 5.0, 2.0 Hz, 1H), 1.93 (td, J=12.0, 10.0 Hz, 1H), 1.36 (d, J=6.0 Hz, 3H).

$^{13}$C NMR (125 MHz, CDCl$_3$): δ 159.5, 138.4, 138.3, 128.6, 128.6, 128.2, 127.9, 127.9, 127.9, 127.0, 127.0, 126.9, 124.4 (q, J$_{C-F}$=269.6 Hz), 124.4 (q, J$_{C-F}$=32.5 Hz), 116.4, 97.0, 83.4, 78.9, 75.5, 71.9, 71.8, 36.7, 18.4.

LRMS (ESI, pos. ion) m/z: calculated for C$_{27}$H$_{27}$F$_3$O$_4$ [M+Na] 495.18. found 495.36.

HRMS (DART, pos. ion) m/z: calculated for C$_{27}$H$_{27}$F$_3$O$_4$ [M+NH$_4$] 490.2200. found 490.2195.

[α]$^{24}$D+33.0 (c 1.00, CH$_2$Cl$_2$).

Example 18

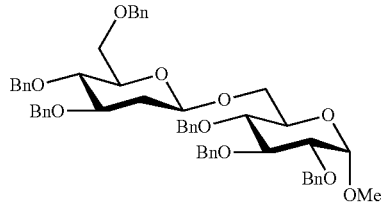

Methyl (3,4,6-tri-O-benzyl-2-deoxy-β-D-glucopyranosyl)-(1→6)-2,3,4-tri-O-benzyl-α-D-glucopyranoside (103a)

A solution of donor 1a (162.8 mg, 0.375 mmol, 1.5 equiv.) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102a (116.1 mg, 0.250 mmol, 1.0 equiv.; see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (20% ethyl acetate in hexanes) to afford disaccharide 103a as a single β-anomer (182.8 mg, 0.208 mmol, 83% yield).

$^1$H NMR (500 MHz, CDCl$_3$): δ 7.39-7.16 (m, 30H), 5.00 (d, J=11.0 Hz, 1H), 4.97 (d, J=11.5 Hz, 2H), 4.82 (d, J=11.0 Hz, 1H), 4.78 (d, J=12.0 Hz, 1H), 4.65 (d, J=12.0 Hz, 2H), 4.62-4.50 (m, 6H), 4.16 (d, J=10.0 Hz, 1H), 4.08 (dd, J=11.0, 1.5 Hz, 1H), 4.00 (t, J=9.5 Hz, 1H), 3.77-3.70 (m, 2H), 3.69-3.65 (m, 1H), 3.60-3.51 (m, 4H), 3.46-3.41 (m, 1H), 3.35 (s, 3H), 3.35-3.30 (m, 1H), 2.19-2.13 (m, 1H), 1.68-1.58 (m, 1H).

$^{13}$C NMR (125 MHz, CDCl$_3$): δ 138.8, 138.4, 138.4, 138.3, 138.3, 138.1, 128.4, 128.4, 128.4, 128.3, 128.3, 128.1, 128.0, 127.9, 127.9, 127.7, 127.6, 127.6, 127.4, 100.0, 98.0, 82.2, 79.7, 79.2, 78.2, 77.4, 75.7, 75.3, 75.0, 74.8, 73.4, 73.3, 71.4, 69.6, 69.4, 67.6, 55.1, 36.5.

LRMS (ESI, pos. ion) m/z: calculated for C$_{55}$H$_{60}$O$_{10}$Na [M+Na] 903.41. found 903.45.

HRMS (ESI, pos. ion) m/z: calculated for C$_{55}$H$_{60}$O$_{10}$Na [M+Na] 903.4084. found 903.4062.

Example 19

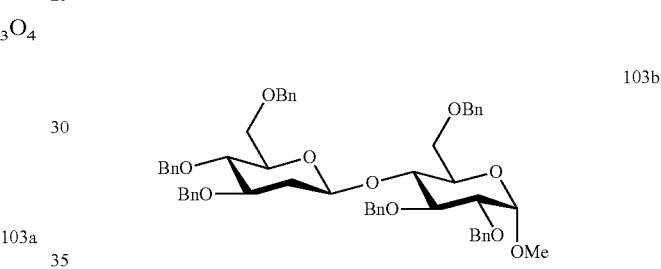

Methyl (3,4,6-tri-O-benzyl-2-deoxy-β-D-glucopyranosyl)-(1→4)-2,3,6-tri-O-benzyl-α-D-glucopyranoside (103b)

A solution of donor 1a (162.8 mg, 0.375 mmol, 1.5 equiv.) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102b (116.1 mg, 0.250 mmol, 1.0 equiv.; see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (10% ethyl acetate in toluene) to afford disaccharide 103b as a single β-anomer (136.6 mg, 0.155 mmol, 62% yield).

$^1$H NMR (500 MHz, CDCl$_3$): δ 7.38-7.16 (m, 30H), 5.02, (d, J=11.0 Hz, 1H), 4.85 (d, J=6.0 Hz, 1H), 4.83 (d, J=6.0 Hz,

1H), 4.76 (d, J=12.0 Hz, 1H), 4.62 (d, J=5.0 Hz, 1H), 4.61-4.56 (m, 3H), 4.53 (d, J=7.5 Hz, 1H), 4.50 (d, J=9.0 Hz, 1H), 4.47 (d, J=2.0 Hz, 1H), 4.46-4.43 (m, 3H), 3.92 (t, J=9.0 Hz, 1H), 3.86 (t, J=9.0 Hz, 1H), 3.75-3.71 (m, 1H), 3.70-3.66 (m, 1H), 3.65-3.56 (m, 3H), 3.52-3.40 (m, 3H), 3.36 (s, 3H), 3.27-3.22 (m, 1H), 2.20 (ddd, J=12.5, 4.5, 1.5 Hz, 1H), 1.57-1.49 (m, 1H).

$^{13}$C NMR (125 MHz, CDCl$_3$): δ 139.4, 138.6, 138.5, 138.4, 138.3, 137.9, 128.5, 128.4, 128.3, 128.2, 128.1, 128.0, 127.8, 127.8, 127.7, 127.7, 127.6, 127.6, 127.4, 127.2, 100.0, 98.3, 80.8, 79.4, 79.3, 78.0, 76.1, 75.5, 75.4, 74.9, 73.6, 73.5, 73.4, 71.4, 69.7, 69.2, 68.6, 55.2, 36.9.

LRMS (ESI, pos. ion) m/z: calculated for C$_{55}$H$_{60}$O$_{10}$Na [M+Na] 903.41. found 903.45.

HRMS (ESI, pos. ion) m/z: calculated for C$_{55}$H$_{60}$O$_{10}$Na [M+Na] 903.4084. found 903.4143.

Example 20

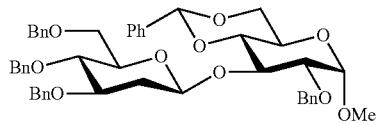

Methyl (3,4,6-tri-O-benzyl-2-deoxy-β-D-glucopyranosyl)-(1→3)-2-O-benzyl-4,6-O-benzylidene-α-D-glucopyranoside (103c)

A solution of donor 1a (162.8 mg, 0.375 mmol, 1.5 equiv.) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102c (93.9 mg, 0.250 mmol, 1.0 equiv.; see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (20% ethyl acetate in hexanes) to afford disaccharide 103c as a single β-anomer (146.0 mg, 0.188 mmol, 74% yield).

$^1$H NMR (500 MHz, CDCl$_3$): δ 7.49-7.44 (m, 2H), 7.38-7.20 (m, 21H), 7.20-7.16 (m, 2H), 5.50 (s, 1H), 4.84 (d, J=10.5 Hz, 1H), 4.76 (dd, J=10.0, 2.0 Hz, 1H), 4.73 (d, J=12.0 Hz, 1H), 4.65 (d, J=12.0 Hz, 1H), 4.61-4.56 (m, 2H), 4.55-4.49 (m, 3H), 4.40 (d, J=12.0 Hz, 1H), 4.23 (dd, J=10.0, 5.0 Hz, 1H), 4.20-4.14 (m, 1H), 3.83-3.76 (m, 1H), 3.72-3.66 (m, 2H), 3.64-3.53 (m, 5H), 3.39 (s, 3H), 3.33-3.28 (m, 1H), 2.37-2.31 (m, 1H), 1.70-1.62 (m, 1H).

$^{13}$C NMR (125 MHz, CDCl$_3$): δ 138.74, 138.60, 138.1, 137.5, 128.9, 128.7, 128.5, 128.4, 128.3, 128.2, 128.1, 127.9, 127.7, 127.7, 127.4, 126.3, 101.5, 101.2, 98.9, 80.3, 79.9, 79.7, 78.1, 77.6, 75.6, 75.1, 73.8, 73.6, 71.6, 69.3, 69.1, 62.7, 55.4, 37.1.

LRMS (ESI, pos. ion) m/z: calculated for C$_{48}$H$_{52}$O$_{10}$Na [M+Na] 811.35. found 811.45.

HRMS (ESI, pos. ion) m/z: calculated for C$_{48}$H$_{52}$O$_{10}$Na [M+Na] 811.3458. found 811.3456.

Example 21

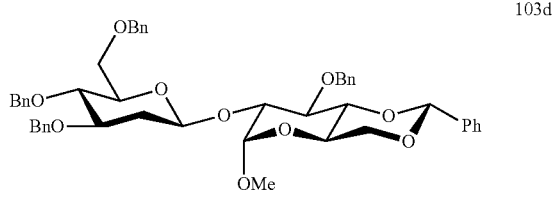

Methyl (3,4,6-tri-O-benzyl-2-deoxy-β-D-glucopyranosyl)-(1→2)-3-O-benzyl-4,6-O-benzylidene-α-D-glucopyranoside (103d)

A solution of donor 1a (162.8 mg, 0.375 mmol, 1.5 equiv.) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102d (93.9 mg, 0.250 mmol, 1.0 equiv. see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (20% ethyl acetate in hexanes) to afford disaccharide 103d as a single β-anomer (126.2 mg, 0.160 mmol, 64% yield).

$^1$H NMR (500 MHz, CDCl$_3$): δ 7.52-7.47 (m, 2H), 7.40-7.23 (m, 21H), 7.22-7.18 (2H), 5.57 (s, 1H), 4.93 (d, J=3.5 Hz, 1H), 4.90 (d, J=11.5 Hz, 1H), 4.88 (d, J=11.0 Hz, 1H), 4.70-4.65 (m, 2H), 4.62-4.58 (m, 2H), 4.57-4.50 (m, 3H), 4.30 (dd, J=10.0, 5.0 Hz, 1H), 4.43 (t, J=9.0 Hz, 1H), 3.90-3.83 (m, 1H), 3.81-3.72 (m, 2H), 3.71-3.67 (m, 2H), 3.62 (t, J=9.5 Hz, 1H), 3.58-3.51 (m, 1H), 3.51-3.46 (m, 1H), 3.43 (s, 3H), 3.38-3.33 (m, 1H), 2.33-2.27 (m, 1H), 1.74-1.65 (m, 1H).

$^{13}$C NMR (125 MHz, CDCl$_3$): δ 138.9, 138.5, 138.5, 138.4, 137.6, 129.1, 128.6, 128.5, 128.5, 128.4, 128.2, 127.9, 127.9, 127.8, 127.8, 127.7, 126.2, 101.8, 101.4, 100.5, 82.6, 79.7, 79.2, 78.7, 78.0, 75.5, 75.2, 75.1, 73.6, 71.6, 69.5, 69.3, 62.4, 55.4, 36.8.

LRMS (ESI, pos. ion) m/z: calculated for C$_{48}$H$_{52}$O$_{10}$Na [M+Na] 811.35. found 811.36.

HRMS (ESI, pos. ion) m/z: calculated for C$_{48}$H$_{52}$O$_{10}$Na [M+Na] 811.3458. found 811.3443.

Example 22

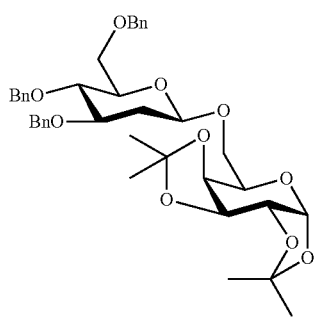

103e 3,4,6-tri-O-benzyl-2-deoxy-β-D-glucopyranosyl)-
(1→6)-1,2:3,4-di-O-isopropylidene-α-D-galactopyranoside (103e A solution of donor 1a (162.8 mg, 0.375 mmol, 1.5 equiv.) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102e (65.1 mg, 0.250 mmol, 1.0 equiv. see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (20% ethyl acetate in hexanes) to afford disaccharide 103e as a single β-anomer (89.7 mg, 0.133 mmol, 53% yield).

$^1$H NMR (500 MHz, $CDCl_3$): δ 7.37-7.22 (m, 13H), 7.21-7.17 (m, 2H), 5.54 (d, J=5.0 Hz, 1H), 4.89 (d, J=12.0 Hz, 1H), 4.70-4.48 (m, 7H), 4.30 (dd, J=5.0, 2.5 Hz, 1H), 4.21 (dd, J=8.0, 2.0 Hz, 1H), 4.08 (dd, J=6.0, 3.0 Hz, 1H), 4.03-3.97 (m, 1H), 3.77-3.69 (m, 2H), 3.69-3.61 (m, 2H), 3.53 (t, J=9.0 Hz, 1H), 3.42-3.37 (m, 1H), 2.45 (dd, J=12.5, 3.5 Hz, 1H), 1.70-1.60 (m, 1H), 1.54 (s, 3H), 1.44 (s, 3H), 1.33 (s, 3H), 1.31 (s, 3H).

$^{13}$C NMR (125 MHz, $CDCl_3$): δ 138.5, 138.4, 128.4, 128.3, 128.0, 127.9, 127.8, 127.6, 127.6, 127.5, 109.3, 108.6, 100.5, 96.4, 79.4, 78.1, 75.2, 74.9, 73.5, 71.5, 71.3, 70.8, 70.5, 69.3, 68.8, 67.8, 36.6, 26.1, 26.0, 25.0, 24.4.

LRMS (ESI, pos. ion) m/z: calculated for $C_{39}H_{48}O_{10}Na$ [M+Na] 699.31. found 699.36.

HRMS (ESI, pos. ion) m/z: calculated for $C_{39}H_{48}O_{10}Na$ [M+Na] 699.3145. found 699.3161.

Example 23

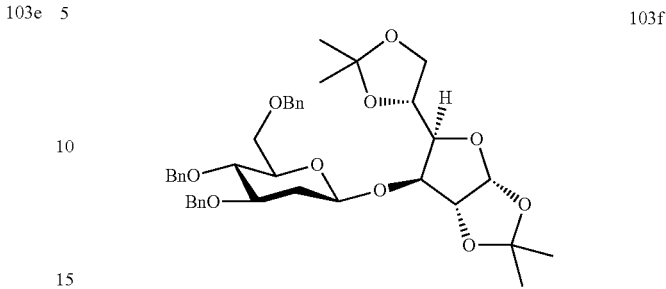

103f 3,4,6-tri-O-benzyl-2-deoxy-β-D-glucopyranosyl)-
(1→3)-1,2:5,6-di-O-isopropylidene-α-D-glucofuranoside (103f A solution of donor 1a (162.8 mg, 0.375 mmol, 1.5 equiv.) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102f (65.1 mg, 0.250 mmol, 1.0 equiv.; see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride ($NH_4Cl$), diluted with water, and extracted with diethyl ether (2×15 mL). The pooled organic phase was washed with brine (2×15 mL) and then dried ($Na_2SO_4$), filtered, and concentrated under reduced pressure. The crude product was purified by silica gel flash column chromatography (17.5% ethyl acetate in hexanes) to afford disaccharide 103f as a single β-anomer (77.8 mg, 0.115 mmol, 46% yield).

$^1$H NMR (500 MHz, $CDCl_3$): δ 7.37-7.21 (m, 15H), 5.92 (d, J=3.5 Hz, 1H), 4.89 (d, J=11.0 Hz, 1H), 4.70-4.53 (m, 6H), 4.50 (d, J=3.5 Hz, 1H), 4.45-4.35 (m, 3H), 4.05 (d, J=3.0 Hz, 1H), 4.04 (d, J=3.0 Hz, 1H), 3.77-3.69 (m, 2H), 3.68-3.61 (m, 1H), 3.58-3.52 (m, 1H), 3.40-3.36 (m, 1H), 2.30-2.24 (m, 1H), 1.65-1.56 (m, 1H), 1.50 (s, 3H), 1.42 (s, 3H), 1.31 (s, 3H), 1.30 (s, 3H).

$^{13}$C NMR (125 MHz, $CDCl_3$): δ 138.4, 138.3, 138.3, 128.4, 128.4, 128.4, 128.0, 127.7, 127.6, 127.6, 111.8, 108.4, 105.1, 97.7, 82.9, 80.4, 79.1, 79.1, 77.9, 75.6, 75.0, 73.6, 71.5, 69.0, 65.8, 36.6, 26.8, 26.5, 26.3, 25.4.

LRMS (ESI, pos. ion) m/z: calculated for $C_{39}H_{48}O_{10}Na$ [M+Na] 699.31. found 699.36.

HRMS (ESI, pos. ion) m/z: calculated for $C_{39}H_{48}O_{10}Na$ [M+Na] 699.3145. found 699.3186.

Example 24

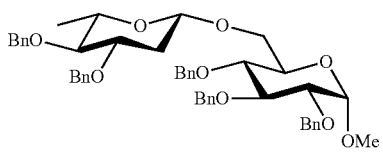

Methyl (3,4-di-O-benzyl-2,6-dideoxy-β-L-arabino-hexopyranosyl)-(1→6)-2,3,4-tri-O-benzyl-α-D-glucopyranoside (104a)

A solution of donor 1b (123.2 mg, 0.375 mmol, 1.5 equiv.; see FIG. 2A) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102a (116.1 mg, 0.250 mmol, 1.0 equiv.; sees FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (20% ethyl acetate in hexanes) to afford disaccharide 104a as a single β-anomer (149.2 mg, 0.193 mmol, 77% yield).

$^1$H NMR (500 MHz, CDCl$_3$): δ 7.40-7.21 (m, 25H), 4.98 (d, J=11.0 Hz, 1H), 4.93 (d, J=11.0 Hz, 1H), 4.88-4.74 (m, 4H), 4.69-4.60 (m, 4H), 4.57 (d, J=11.5 Hz, 1H), 4.46 (dd, J=9.5, 1.5 Hz, 1H), 4.23 (dd, J=11.0, 3.0 Hz, 1H), 3.98 (t, J=9.0 Hz, 1H), 3.73-3.69 (m, 1H), 3.68-3.57 (m, 3H), 3.54 (dd, J=9.5, 1.5 Hz, 1H), 3.35 (s, 3H), 3.35-3.29 (m, 1H), 3.10 (t, J=9.0 Hz, 1H), 2.42-2.37 (m, 1H), 1.61 (td, J=12.0, 10.0 Hz, 1H), 1.27 (d, J=6.5 Hz, 3H).

$^{13}$C NMR (125 MHz, CDCl$_3$): δ 138.9, 138.5, 138.3, 138.2, 128.4, 128.4, 128.4, 128.4, 128.3, 128.2, 128.1, 128.0, 128.9, 128.9, 128.7, 128.6, 128.6, 99.3, 98.2, 837, 82.0, 79.8, 79.1, 77.5, 75.8, 75.2, 75.0, 73.4, 71.4, 71.2, 69.9, 66.6, 55.1, 36.9, 18.2.

LRMS (ESI, pos. ion) m/z: calculated for C$_{48}$H$_{54}$O$_9$Na [M+Na] 797.37. found 797.36.

HRMS (ESI, pos. ion) m/z: calculated for C$_{48}$H$_{54}$O$_9$Na [M+Na] 797.3665. found 797.3663.

Example 25

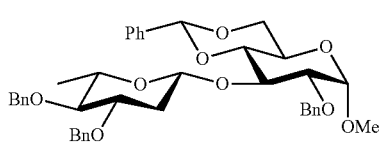

Methyl (3,4-di-O-benzyl-2,6-dideoxy-β-L-arabino-hexopyranosyl)-(1→3)-2-O-benzyl-4,6-O-benzylidene-α-D-glucopyranoside (104c)

A solution of donor 1b (123.2 mg, 0.375 mmol, 1.5 equiv.; see FIG. 2A) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102c (93.9 mg, 0.250 mmol, 1.0 equiv.; see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (5% ethyl acetate in toluene) to afford disaccharide 104c as a single β-anomer (116.1 mg, 0.170 mmol, 68% yield).

$^1$H NMR (500 MHz, CDCl$_3$): δ 7.47-7.40 (m, 4H), 7.36-7.24 (m, 16H), 5.52 (s, 1H), 4.96-4.90 (m, 2H), 4.80 (dd, J=10.0, 2.0 Hz, 1H), 4.74 (d, J=7.0 Hz, 1H), 4.66-4.62 (m, 2H), 4.58 (d, J=12.0 Hz, 1H), 4.48 (d, J=12.0 Hz, 1H), 4.29-4.24 (m, 2H), 3.81 (td, J=10.0, 4.5 Hz, 1H), 3.72-3.67 (m, 1H), 3.58-3.48 (m, 3H), 3.39 (s, 3H), 3.35-3.28 (m, 1H), 3.16-3.11 (m, 1H), 2.48 (ddd, J=12.0, 10.0, 1.5 Hz, 1H), 1.61 (td, J=12.0, 10.0 Hz, 1H), 1.34 (d, J=6.0 Hz, 3H).

$^{13}$C NMR (125 MHz, CDCl$_3$): δ 138.5, 138.5, 138.5, 137.4, 129.0, 128.4, 128.4, 128.3, 128.3, 128.2, 128.1, 127.7, 127.6, 127.6, 125.8, 101.3, 100.8, 99.7, 83.8, 81.9, 79.5, 77.8, 77.3, 75.2, 73.8, 71.5, 71.2, 69.1, 62.0, 55.3, 37.3, 18.3.

LRMS (ESI, pos. ion) m/z: calculated for C$_{41}$H$_{46}$O$_9$Na [M+Na] 705.30. found 705.36.

HRMS (ESI, pos. ion) m/z: calculated for C$_{41}$H$_{46}$O$_9$Na [M+Na] 705.3040. found 705.3046.

Example 26

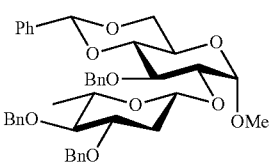

Methyl (3,4-di-O-benzyl-2,6-dideoxy-β-L-arabino-hexopyranosyl)-(1→2)-3-O-benzyl-4,6-O-benzylidene-α-D-glucopyranoside (104d)

A solution of donor 1b (123.2 mg, 0.375 mmol, 1.5 equiv.; see FIG. 2A) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.).

After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102d (93.9 mg, 0.250 mmol, 1.0 equiv., see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (20% ethyl acetate in hexanes) to afford disaccharide 104d as a single β-anomer (119.5 mg, 0.175 mmol, 70% yield).

$^1$H NMR (500 MHz, CDCl$_3$): δ 7.53-7.46 (m, 2H), 7.45-7.40 (m, 2H), 7.40-7.21 (m, 16H), 5.55 (s, 1H), 4.95 (d, J=10.5 Hz, 1H), 4.89-4.78 (m, 3H), 4.66 (d, 11.0 Hz, 2H), 4.62 (d, J=12.0 Hz, 1H), 4.54 (d, J=11.5 Hz, 1H), 4.29 (dd, J=10.0, 4.5 Hz, 1H), 4.40 (d, J=9.5, 3.5 Hz, 1H), 3.93 (t, J=9.0 Hz, 1H), 3.84 (td, J=10.0, 4.5 Hz, 1H), 3.76-3.70 (m, 1H), 3.66-3.58 (m, 2H), 3.43 (s, 3H), 3.37-3.30 (m, 1H), 3.13 (t, J=9.0 Hz, 1H), 2.35 (dd, J=12.5, 3.5 Hz, 1H), 1.77-1.69 (m, 1H), 1.32 (d, J=6.0 Hz, 3H).

$^{13}$C NMR (125 MHz, CDCl$_3$): δ 139.0, 138.5, 138.4, 137.5, 128.9, 128.4, 128.4, 128.2, 128.1, 128.1, 128.0, 127.7, 127.7, 127.6, 127.4, 126.1, 101.3, 98.9, 97.3, 83.6, 81.7, 79.2, 77.1, 75.7, 75.2, 75.0, 71.8, 71.2, 69.1, 62.4, 55.2, 36.6, 18.3.

LRMS (ESI, pos. ion) m/z: calculated for C$_{41}$H$_{46}$O$_9$Na [M+Na] 705.31. found 705.36.

HRMS (ESI, pos. ion) m/z: calculated for C$_{41}$H$_{46}$O$_9$Na [M+Na] 705.3040. found 705.3016.

Example 27

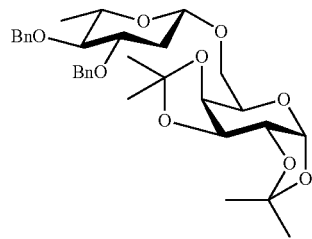

104e 3,4-di-O-benzyl-2,6-dideoxy-β-L-arabinohexopyranosyl)-(1→6)-1,2:3,4-di-O-isopropylidene-α-D-galactopyranoside (104e A solution of donor 1b (123.2 mg, 0.375 mmol, 1.5 equiv.; see FIG. 2A) and 2,4,6-tri-tert-butylpyrimidine (TTBP, 93.2 mg, 0.375 mmol, 1.5 equiv.) in 3.0 mL THF was cooled to −78° C. and treated dropwise with potassium hexamethyldisilazane (1 M in THF, 0.375 mL, 0.375 mmol, 1.5 equiv.). After 15 minutes, a solution of p-toluenesulfonic anhydride (122.4 mg, 0.375 mmol, 1.5 equiv.) in 2.0 mL THF was added rapidly to the reaction. The solution was maintained at −78° C. for 30 min. Acceptor 102e (65.1 mg, 0.250 mmol, 1.0 equiv.; see FIG. 2B) was dissolved in 2.0 mL THF, cooled to −78° C., and treated with potassium hexamethyldisilazane (0.250 mL, 0.250 mmol, 1.0 equiv.). After 15 minutes, this solution was transferred dropwise by syringe to the primary reaction vessel. The reaction mixture was then allowed to gradually warm to room temperature over the course of 3 h, and stirred for an additional 15 h. The reaction was quenched with several drops of saturated, aqueous ammonium chloride (NH$_4$Cl), diluted with water, and extracted with diethyl ether (2×15 mL). The pooled organic phase was washed with brine (2×15 mL) and then dried (Na$_2$SO$_4$), filtered, and concentrated under reduced pressure. The crude product was purified by silica gel flash column chromatography (7.5% ethyl acetate in toluene) to afford disaccharide 104e as a single β-anomer (65.6 mg, 0.115 mmol, 46% yield).

$^1$H NMR (500 MHz, CDCl$_3$): δ 7.35-7.25 (m, 10H), 5.51 (d, J=5.0 Hz, 1H), 4.94 (d, J=11.0 Hz, 1H), 4.70-4.63 (m, 2H), 4.62 (m, 2H), 4.47 (dd, J=9.5, 1.5 Hz, 1H), 4.33-4.29 (m, 2H), 4.05-4.00 (m, 1H), 3.86 (dd, J=10.0, 6.0 Hz, 1H), 3.76 (dd, J=10.0, 8.5 Hz, 1H), 3.64-3.58 (m, 1H), 3.35-3.29 (m, 1H), 3.12 (t, J=9.0 Hz, 1H), 2.39-2.34 (m, 1H), 1.66-1.58 (m, 1H), 1.52 (s, 3H), 1.44 (s, 3H), 1.35 (s, 3H), 1.32 (s, 3H), 1.31 (d, J=6.0 Hz, 3H).

$^{13}$C NMR (125 MHz, CDCl$_3$): δ 138.5, 138.4, 128.4, 128.4, 128.1, 127.7, 127.6, 109.2, 108.5, 100.2, 96.4, 83.7, 79.3, 75.2, 71.4, 71.4, 70.8, 70.6, 67.5, 65.9, 36.9, 26.1, 26.0, 24.9, 24.5, 18.2.

LRMS (ESI, pos. ion) m/z: calculated for C$_{32}$H$_{42}$O$_9$Na [M+Na] 593.27. found 593.36.

HRMS (ESI, pos. ion) m/z: calculated for C$_{32}$H$_{42}$O$_9$Na [M+Na] 593.2727. found 593.2744.

Example 28

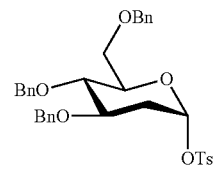

p-Toluenesulfonyl 3,4,6-tri-O-benzyl-2-deoxy-α-D-glucopyranoside

A solution of donor 1a (21.7 mg, 0.050 mmol, 1.0 equiv.) and 2,4,6-tri-tert-butylpyrimidine (TTBP, 13.0 mg, 0.050 mmol, 1.0 equiv.) in 0.50 mL THF-d$_8$ was cooled to −78° C. in a dry ice/acetone bath and treated dropwise with potassium hexamethyldisilazane (1 M in THF, 50.0 μL, 0.050 mmol, 1.0 equiv.). After 15 minutes, a solution of p-toluenesulfonic anhydride (17.1 mg, 0.053 mmol, 1.05 equiv.) in 0.50 mL THF-d$_8$ was added rapidly to the reaction. The reaction was maintained at −78° C. for 30 min, transferred by syringe to a pre-cooled 5 mm Low Pressure/Vacuum Valve NMR tube, and promptly inserted into the NMR instrument probe pre-cooled to −78° C. for $^1$H NMR, $^{13}$C NMR, and 2D-Gradient HSQC data acquisition. The temperature was maintained for 2 hours, then warmed by 10 degrees every 10 minutes. At each 10 minute interval, the $^1$H NMR spectrum was recorded. At −78° C., a single compound was present in the spectrum. At −5° C., the spectrum began to show trace elimination of the tosylate to the corresponding glucal. Significant glucal was present at 25-78° C.

¹H NMR (500 MHz, CDCl₃): δ 7.78 (d, J=8.0 Hz, 2H), 6.11 (bs, 1H), 4.90 (d, J=10.5 Hz, 1H), 4.70 (d, J=12.0 Hz, 1H), 4.60 (d, J=12.0 Hz, 1H), 4.50 (d, J=11.0 Hz, 1H), 4.40-4.32 (m, 1H), 3.82-3.75 (m, 1H), 3.31 (d, J=9.0 Hz, 1H), 2.98 (d, J=10.0 Hz, 1H), 2.60-2.52 (m, 1H), 2.49 (d, J=10.0 Hz, 1H), 2.28 (s, 3H).

¹³C NMR (125 MHz, CDCl₃): δ 102.3, 77.5, 77.1, 75.9, 73.7, 73.4, 71.4, 35.3, 21.6.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method of forming a glycosidic bond, comprising:
   combining a first solvent, a reducing sugar, and a first strong Bronsted base, thereby forming a first reaction mixture;
   combining a sulfonylating agent and the first reaction mixture, thereby forming a glycosyl sulfonate;
   combining a second solvent, a glycosyl acceptor, and a second strong Bronsted base, thereby forming a second reaction mixture; and
   combining the glycosyl sulfonate and the second reaction mixture, thereby forming a glycosidic bond;
   wherein the reducing sugar is a pyranose; the sulfonylating agent is selected from the group consisting of tosyl 4-nitroimidazole, benzenesulfonyl 4-nitroimidazole, and p-toluenesulfonic anhydride; and the glycosidic bond is formed with greater than or equal to 90% stereoselectivity for a β linkage.

2. The method of claim 1, wherein the glycosidic bond is formed with greater than or equal to 95% stereoselectivity for a β linkage.

3. The method of claim 1, wherein the reducing sugar is a 2-deoxy sugar.

4. The method of claim 1, wherein the reducing sugar is a D-sugar.

5. The method of claim 1, wherein the reducing sugar is an L-sugar.

6. The method of claim 1, wherein the first strong Bronsted base is non-nucleophilic.

7. The method of claim 1, wherein the second strong Bronsted base is non-nucleophilic.

8. The method of claim 1, wherein the first strong Bronsted base is non-nucleophilic; and the second strong Bronsted base is non-nucleophilic.

9. The method of claim 1, wherein the first strong Bronsted base is selected from the group consisting of: alkali metal alkoxides, alkali metal amides, alkaline earth metal alkoxides, and alkaline earth metal amides.

10. The method of claim 1, wherein the first strong Bronsted base is selected from the group consisting of: sodium tert-butoxide, potassium tert-butoxide, lithium tert-butoxide, lithium diisopropylamide, lithium tetramethylpiperidide, sodium hexamethyldisilazane (NaHMDS), and potassium hexamethyldisilazane (KHMDS).

11. The method of claim 1, wherein the second strong Bronsted base is selected from the group consisting of: alkali metal alkoxides, alkali metal amides, alkaline earth metal alkoxides, and alkaline earth metal amides.

12. The method of claim 1, wherein the second strong Bronsted base is selected from the group consisting of: sodium tert-butoxide, potassium tert-butoxide, lithium tert-butoxide, lithium diisopropylamide, lithium tetramethylpiperidide, sodium hexamethyldisilazane (NaHMDS), and potassium hexamethyldisilazane (KHMDS).

13. The method of claim 1, wherein the first strong Bronsted base is same as the second strong Bronsted base.

14. The method of claim 1, wherein the first reaction mixture further comprises tri-tert-butylpyrimidine (TTBP).

15. The method of claim 1, wherein the glycosyl acceptor comprises an alcohol, a thiol, or an amine.

16. The method of claim 1, wherein the glycosyl acceptor is a monosaccharide, a disaccharide, an oligosaccharide, or a polysaccharide, each comprising at least one —OH, —SH, or primary or secondary amino group.

17. The method of claim 1, wherein the first solvent is selected from the group consisting of tetrahydrofuran (THF), diglyme, and a combination of THF and diglyme.

18. The method of claim 1, wherein the second solvent is selected from the group consisting of tetrahydrofuran (THF), diglyme, and a combination of THF and diglyme.

19. The method of claim 1, wherein the first solvent is the same as the second solvent.

20. The method of claim 1, wherein the sulfonylating agent is tosyl 4-nitroimidazole.

21. The method of claim 1, wherein the sulfonylating agent is benzenesulfonyl 4-nitroimidazole.

22. The method of claim 1, wherein the sulfonylating agent is p-toluenesulfonic anhydride.

* * * * *